US008213697B2

(12) United States Patent
Takakura et al.

(10) Patent No.: US 8,213,697 B2
(45) Date of Patent: Jul. 3, 2012

(54) AGGLUTINATION IMAGE AUTOMATIC JUDGING METHOD BY MT SYSTEM, DEVICE, PROGRAM, AND RECORDING MEDIUM

(75) Inventors: Toshiaki Takakura, Sunto-gun (JP); Tetsunori Shibuya, Hachioji (JP)

(73) Assignee: Beckman Coulter, Inc., Brea, CA (US)

( * ) Notice: Subject to any disclaimer, the term of this patent is extended or adjusted under 35 U.S.C. 154(b) by 218 days.

(21) Appl. No.: 12/646,497

(22) Filed: Dec. 23, 2009

(65) Prior Publication Data

US 2010/0119132 A1 May 13, 2010

Related U.S. Application Data

(63) Continuation of application No. PCT/JP2008/061663, filed on Jun. 26, 2008.

(30) Foreign Application Priority Data

Jun. 29, 2007 (JP) .................................. 2007-173149

(51) Int. Cl.
 *G06K 9/00* (2006.01)
(52) U.S. Cl. ........................................ 382/128; 382/131
(58) Field of Classification Search .................. 382/128, 382/133, 134, 131; 356/39; 435/7.1
 See application file for complete search history.

(56) References Cited

U.S. PATENT DOCUMENTS

| | | | | |
|---|---|---|---|---|
| 4,575,492 A | * | 3/1986 | David et al. | 436/164 |
| 5,192,692 A | * | 3/1993 | Sakai et al. | 436/165 |
| 5,768,407 A | * | 6/1998 | Shen et al. | 382/133 |
| 7,758,811 B2 | * | 7/2010 | Durack et al. | 422/73 |
| 7,799,569 B2 | * | 9/2010 | Durak et al. | 436/63 |
| 7,943,384 B2 | * | 5/2011 | Durack et al. | 436/63 |

FOREIGN PATENT DOCUMENTS

| | | |
|---|---|---|
| JP | 03-108638 A | 5/1991 |
| JP | 04-072547 A | 3/1992 |
| JP | 07-325116 A | 12/1995 |
| JP | 08-210790 A | 8/1996 |
| JP | 08-210970 | * 10/1996 |
| JP | 09-145594 A | 6/1997 |
| JP | 2004-187562 | * 12/2002 |
| JP | 2004-187562 A | 7/2004 |

OTHER PUBLICATIONS

Machine Translation of JP 08210970; Kitagawa et al Oct. 24, 2011.*
International Search Report from PCT/JP2008/061663, mailed Sep. 22, 2008 (3 pages; English Translation, p. 1, Japanese, pp. 2-3).

* cited by examiner

*Primary Examiner* — Vikkram Bali
*Assistant Examiner* — Nancy Bitar
(74) *Attorney, Agent, or Firm* — Kilpatrick Townsend & Stockton LLP

(57) ABSTRACT

The present invention include a method of determining an agglutination pattern type of a pattern formed in a reaction vessel, comprising setting a reference space based on one or a plurality of types of typical reaction images setting one or a plurality of types of unit regions in each of the reference spaces and determining a Mahalanobis distance for each unit region setting a threshold value from each of the Mahalanobis distances obtained setting one or a plurality of unit regions for a reaction image as an object image and determining the Mahalanobis distance, and (E) determining a pattern type for the object image by comparing the threshold value with the distances.

33 Claims, 25 Drawing Sheets

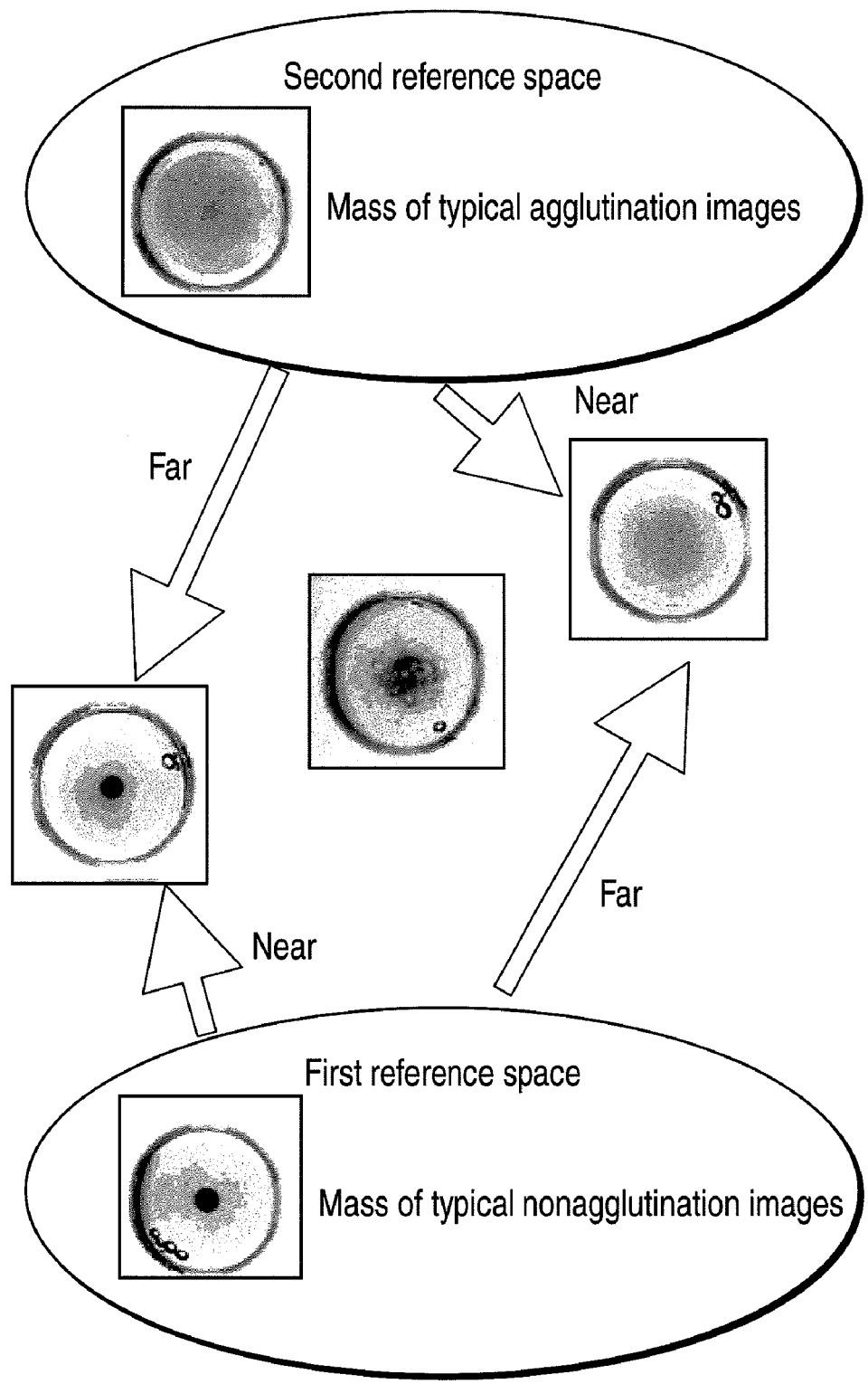
F I G. 1

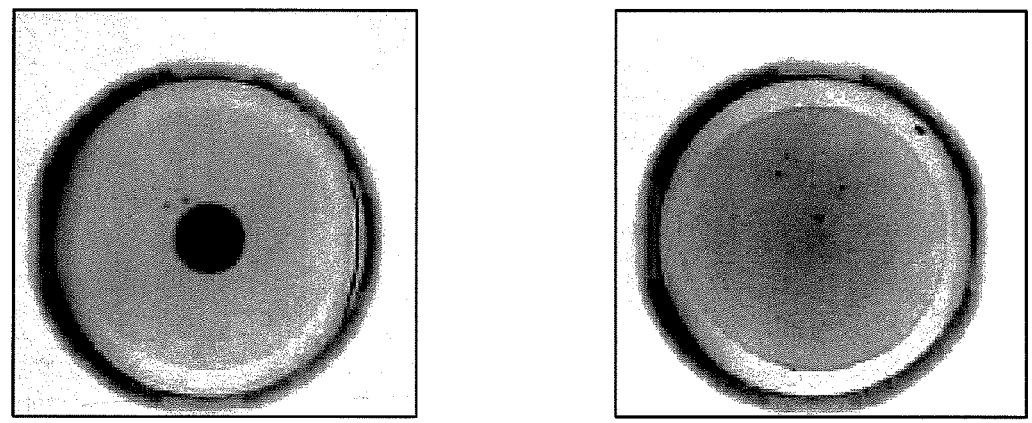
(A)            (B)
F I G. 3
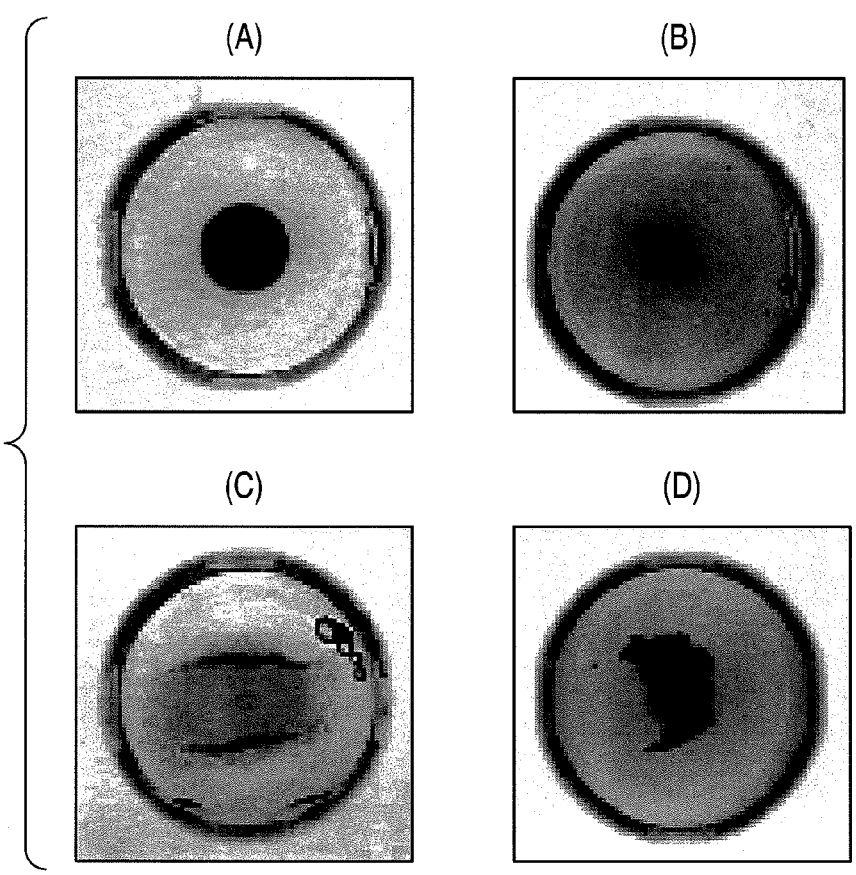
F I G. 4

Mean value M $$M_1 = \frac{1}{50}(X_{1,1} + X_{2,1} + \cdots + X_{50,1})$$

$$M_2 = \frac{1}{50}(X_{1,2} + X_{2,2} + \cdots + X_{50,2})$$

$$\vdots$$

$$M_{5625} = \frac{1}{50}(X_{1,5625} + X_{2,5625} + \cdots + X_{50,5625})$$

Equation (1)

Linear formula L $$L_1 = M_1 X_{1,1} + M_2 X_{1,2} + \cdots + M_{5625} X_{1,5625}$$

$$L_2 = M_1 X_{2,1} + M_2 X_{2,2} + \cdots + M_{5625} X_{2,5625}$$

$$\vdots$$

$$L_{50} = M_1 X_{50,1} + M_2 X_{50,2} + \cdots + M_{5625} X_{50,5625}$$

Equation (2)

FIG. 9

Intuitive meaning of $S_T(i)$, $S_\beta(i)$, $V(i)$
Meaning of $S_T(i)$
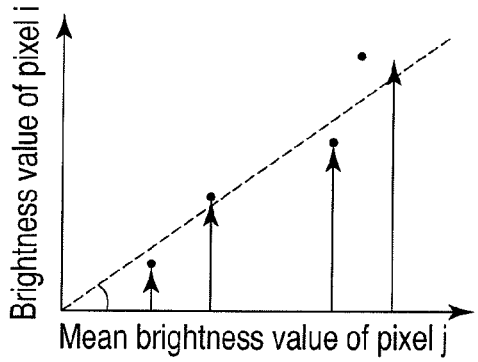
(A)
Meaning of $S_\beta(i)$
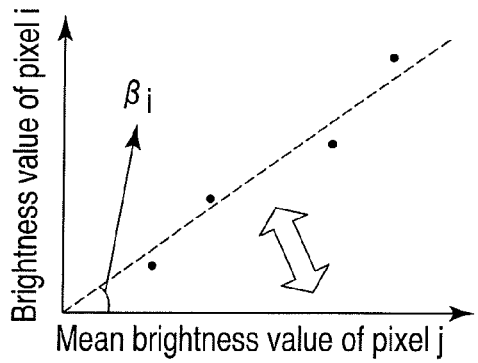
(B)
Meaning of $V(i)$
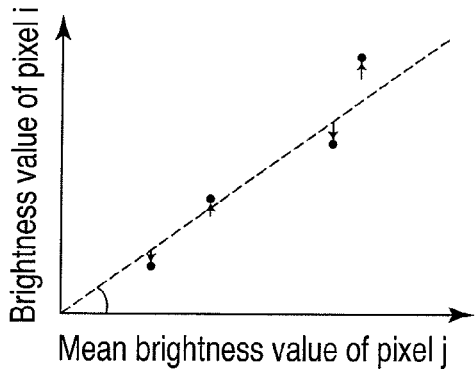
(C)
$S_T(i)$: Square sum of all values indicated by ↑
$S_\beta(i)$: Change in regression line
$V(i)$: Freedom magnitude of each value indicated by ↑
FIG. 10

|  | Area1 | | Area2 | |
|---|---|---|---|---|
|  | $Y_1$ | $Y_2$ | $Y_1$ | $Y_2$ |
| 1 | $Y_{1,1}$ | $Y_{1,2}$ | $Y_{1,1}$ | $Y_{1,2}$ |
| 2 | $Y_{2,1}$ | $Y_{2,2}$ | $Y_{2,1}$ | $Y_{2,2}$ |
| ⋮ | ⋮ | ⋮ | ⋮ | ⋮ |
| 50 | $Y_{50,1}$ | $Y_{50,2}$ | $Y_{50,1}$ | $Y_{50,2}$ |
| Mean | $m_1$ | $m_2$ | $m_1$ | $m_2$ |

Data of $Y_1$, $Y_2$ in Areas 1 and 2

F I G. 11

|  | Nonagglutination image | | Agglutination image | |
|---|---|---|---|---|
|  | Area1 | Area2 | Area1 | Area2 |
|  | $D_1$ | $D_2$ | $D_1$ | $D_2$ |
| 1 | $D_{1,1}$ | $D_{2,1}$ | $D_{1,1}$ | $D_{1,2}$ |
| 2 | $D_{2,2}$ | $D_{2,2}$ | $D_{2,1}$ | $D_{2,2}$ |
| ⋮ | ⋮ | ⋮ | ⋮ | ⋮ |
| 50 | $D_{50,2}$ | $D_{50,2}$ | $D_{50,1}$ | $D_{50,2}$ |

Four composite distances of images used in reference spaces

F I G. 12

| Pixel No. \ Pixel position $X'_j$ | $X'_1$ | $X'_2$ | ... | $X'_{75}$ | $X'_{76}$ | ... | $X'_{5625}$ | Linear formula |
|---|---|---|---|---|---|---|---|---|
| 1 | $X'_{1,1}$ | $X'_{1,2}$ | ... | $X'_{1,75}$ | $X'_{1,76}$ | ... | $X'_{1,5625}$ | $L'_1$ |
| 2 | $X'_{2,1}$ | $X'_{2,2}$ | ... | $X'_{2,75}$ | $X'_{2,76}$ | ... | $X'_{2,5625}$ | $L'_2$ |
| ⋮ | ⋮ | ⋮ | ⋮ | ⋮ | ⋮ | ⋮ | ⋮ | ⋮ |
| k | $X'_{k,1}$ | $X'_{k,2}$ | ... | $X'_{k,75}$ | $X'_{k,76}$ | ... | $X'_{k,5625}$ | $L'_k$ |

Brightness value data of object image (A)

Linear formula L'

$$L'_1 = M_1 X'_{1,1} + M_2 X'_{1,2} + \cdots + M_{5625} X'_{1,5625}$$
$$L'_2 = M_1 X'_{2,1} + M_2 X'_{2,2} + \cdots + M_{5625} X'_{2,5625}$$
$$\vdots$$
$$L'_k = M_1 X'_{50,1} + M_2 X'_{50,2} + \cdots + M_{5625} X'_{50,5625}$$

Equation (3)

(B)

F I G. 14

|  | Nonagglutination image | | Agglutination image | |
| --- | --- | --- | --- | --- |
|  | Area1 | Area2 | Area1 | Area2 |
|  | $D'_1$ | $D'_2$ | $D'_1$ | $D'_2$ |
| 1 | $D'_{1,1}$ | $D'_{1,2}$ | $D'_{1,1}$ | $D'_{1,2}$ |
| 2 | $D'_{2,2}$ | $D'_{2,2}$ | $D'_{2,1}$ | $D'_{2,2}$ |
| ⋮ | ⋮ | ⋮ | ⋮ | ⋮ |
| k | $D'_{k,1}$ | $D'_{k,2}$ | $D'_{k,1}$ | $D'_{k,2}$ |

Distance from reference spaces

F I G. 15

Signal-to-noise ratio $\eta_i$ of ith member is $$\beta_i = \frac{L_i}{r} \qquad (i=1,2,\cdots,n) \quad (53.17)$$

$$\eta_i = \frac{2r}{V_i} \qquad (i=1,2,\cdots,n) \quad (53.18)$$

wherein $$L_i = M_1 X_{1i} + \cdots + M_k X_{ki} \qquad (i=1,2,\cdots,k) \quad (53.19)$$

$$r = M_1^2 + M_2^2 + \cdots + M_k^2 \qquad (53.20)$$

$$S_T(i) = X_{1i}^2 + X_{2i}^2 + \cdots + X_{ki}^2 \qquad (f=k) \;\; (i=1,2,\cdots,k) \quad (53.21)$$

$$S_\beta(i) = \frac{L_i^2}{r} \qquad (f=1) \;\; (i=1,2,\cdots,k) \quad (53.22)$$

$$V_i = \frac{1}{k-1}[S_T(i) - S_\beta(i)] \qquad (53.23)$$

F I G. 16

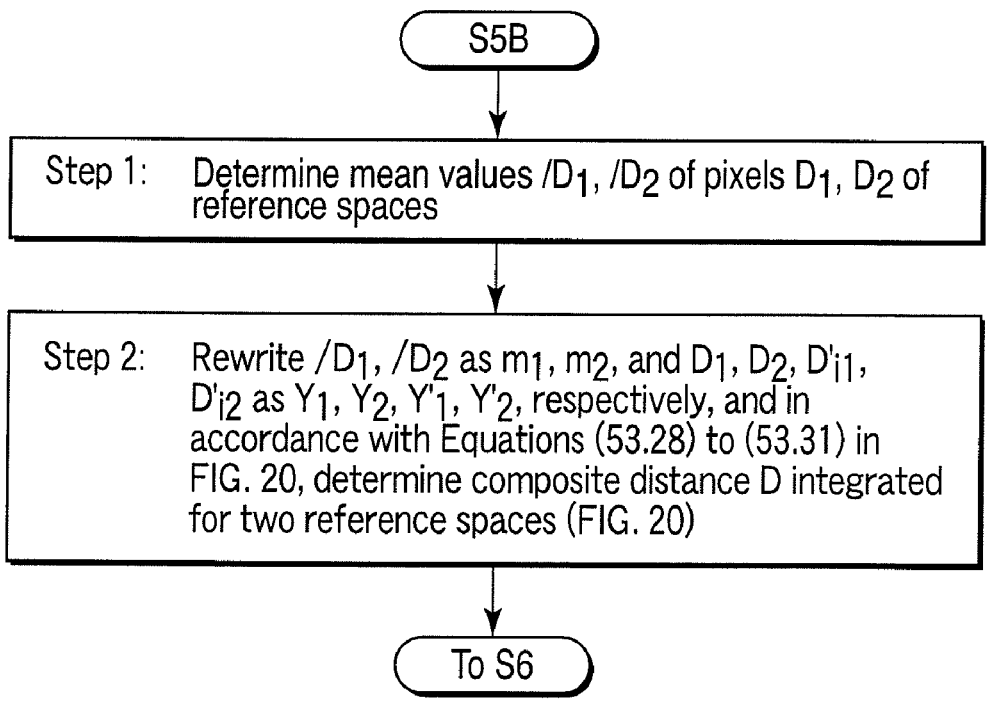

$$\begin{cases} Y_{1i} = \beta_i & (i=1,2,\cdots,n) \quad (53.24) \\ Y_{2i} = \sqrt{\dfrac{1}{\eta_i}} & (i=1,2,\cdots,n) \quad (53.25) \end{cases}$$

FIG. 17

Flow 5B

S5B

Step 1: Determine mean values $/D_1$, $/D_2$ of pixels $D_1$, $D_2$ of reference spaces Step 2: Rewrite $/D_1$, $/D_2$ as $m_1$, $m_2$, and $D_1$, $D_2$, $D'_{i1}$, $D'_{i2}$ as $Y_1$, $Y_2$, $Y'_1$, $Y'_2$, respectively, and in accordance with Equations (53.28) to (53.31) in FIG. 20, determine composite distance D integrated for two reference spaces (FIG. 20)

| | Nonagglutination image | | | Agglutination image | | |
|---|---|---|---|---|---|---|
| | Area1 | Area2 | Integrated composite distance | Area1 | Area2 | Integrated composite distance |
| | $D_1$ | $D_2$ | $D$ | $D_1$ | $D_2$ | $D$ |
| 1 | $D_{1,1}$ | $D_{1,2}$ → $D_1$ | | $D_{1,1}$ | $D_{1,2}$ → $D_1$ | |
| 2 | $D_{2,1}$ | $D_{2,2}$ → $D_2$ | | $D_{2,1}$ | $D_{2,2}$ → $D_2$ | |
| . | . | . | . | . | . | . |
| . | . | . | . | . | . | . |
| . | . | . | . | . | . | . |
| 50 | $D_{50,1}$ | $D_{50,2}$ → $D_{50}$ | | $D_{50,1}$ | $D_{50,2}$ → $D_{50}$ | |

Integrated composite distance for reference spaces (A)

| | Nonagglutination image | | | Agglutination image | | |
|---|---|---|---|---|---|---|
| | Area1 | Area2 | Integrated composite distance | Area1 | Area2 | Integrated composite distance |
| | $D'_1$ | $D'_2$ | $D'$ | $D'_1$ | $D'_2$ | $D'$ |
| 1 | $D'_{1,1}$ | $D'_{1,2}$ → $D'_1$ | | $D'_{1,1}$ | $D'_{1,2}$ → $D'_1$ | |
| 2 | $D'_{2,1}$ | $D'_{2,2}$ → $D'_2$ | | $D'_{2,1}$ | $D'_{2,2}$ → $D'_2$ | |
| . | . | . | . | . | . | . |
| . | . | . | . | . | . | . |
| . | . | . | . | . | . | . |
| k | $D'_{k,1}$ | $D'_{k,2}$ → $D'_k$ | | $D'_{k,1}$ | $D'_{k,2}$ → $D'_k$ | |

Integrated composite distance for object image (B)

F I G. 19

$$V = \begin{pmatrix} V_{11} & V_{12} \\ V_{21} & V_{22} \end{pmatrix} \quad (53.28)$$

Wherein $$V_{11} = \frac{1}{n-1}[(Y_{1.1}-m_1)^2 + \cdots + (Y_{1.2}-m_1)^2] \quad (53.29)$$

$$V_{12} = V_{21} = \frac{1}{n-1}[(Y_{1.1}-m_1)(Y_{1.2}-m_2) + \cdots + (Y_{50.1}-m_1)(Y_{50.2}-m_2)]^2$$

$$V_{22} = \frac{1}{n-1}[(Y_{1.2}-m_2)^2 + \cdots + (Y_{50.2}-m_2)^2]$$

Cofactor matrix A of fractional matrix V is $$A = \begin{pmatrix} V_{22} & -V_{12} \\ -V_{21} & V_{11} \end{pmatrix} \quad (53.30)$$

Therefore, from MTA method, the square of the distance $D_i$ of the member in reference space is given as $$D_i^2 = V_{22} \times (Y_{1i}-m_1)^2 - V_{12}(Y_{1i}-m_1)(Y_{2i}-m_2) - V_{21}(Y_{1i}-m_1)(Y_{2i}-m_2) + V_{11}(Y_{2i}-m_2)^2$$

$$(i=1,2,\cdots,n) \quad (53.31)$$

$D_1, D_2, \cdots D_n$ are distances from zero point $(m_1, m_2)$ $$\beta_i = \frac{L}{r} \quad (53.32)$$

$$\eta_i = \frac{2r}{\sqrt{N}} \quad (53.33)$$

$$Y_{1i}' = \beta_i \quad (53.34)$$

$$Y_{2i}' = \sqrt{\frac{1}{\eta_i}} \quad (53.35)$$

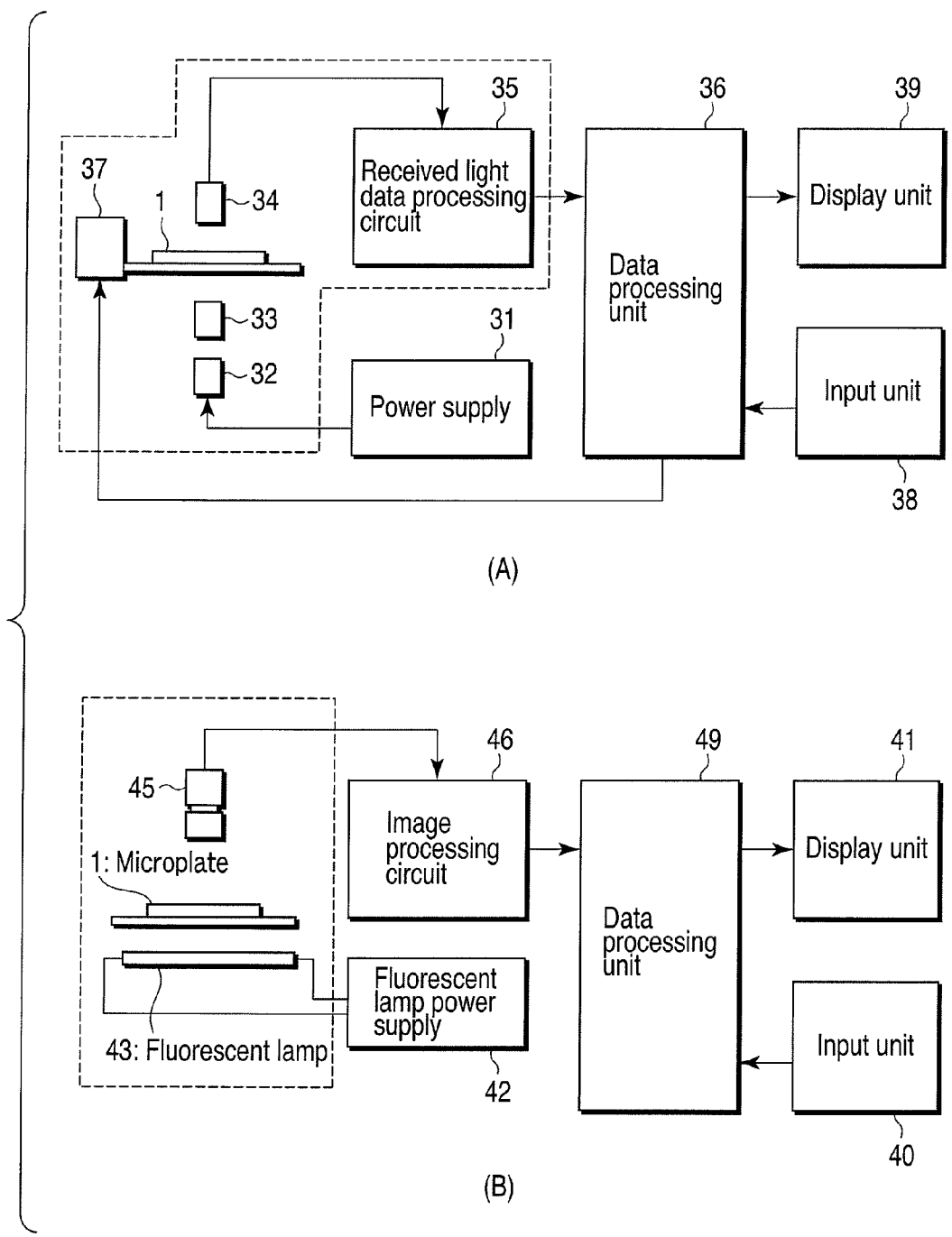
F I G. 21

| Second reference space (agglutination image) | | First reference space (nonagglutination image) | |
|---|---|---|---|
| Agglutination 1 | 1.48E−05 | Agglutination 1 | 2.18E−05 |
| Agglutination 2 | 2.26E−05 | Agglutination 2 | 2.20E−05 |
| ⋮ | ⋮ | ⋮ | ⋮ |
| Agglutination 50 | 1.86E−05 | Agglutination 50 | 3.03E−05 |
| Nonagglutination 1 | 5.80E−05 | Nonagglutination 1 | 7.40E−06 |
| Nonagglutination 2 | 5.87E−05 | Nonagglutination 2 | 6.70E−06 |
| ⋮ | ⋮ | ⋮ | ⋮ |
| Nonagglutination 50 | 8.34E−05 | Nonagglutination 50 | 2.73E−06 |

Composite distance of image in reference spaces (A)

| | Second reference space | First reference space |
|---|---|---|
| Nonagglutination | 9.47E−05 | 1.39E−05 |
| Agglutination | 4.01E−05 | 3.12E−05 |
| Weak agglutination | 1.85E−05 | 3.12E−05 |
| Milky fluid | 4.99E−05 | 2.45E−05 |
| Dropoff | 1.08E−05 | 2.65E−05 |
| Deformation | 6.28E−05 | 3.28E−05 |
| Foreign matter | 9.06E−05 | 4.16E−05 |

Composite distance of image in reference spaces (B)

FIG. 23

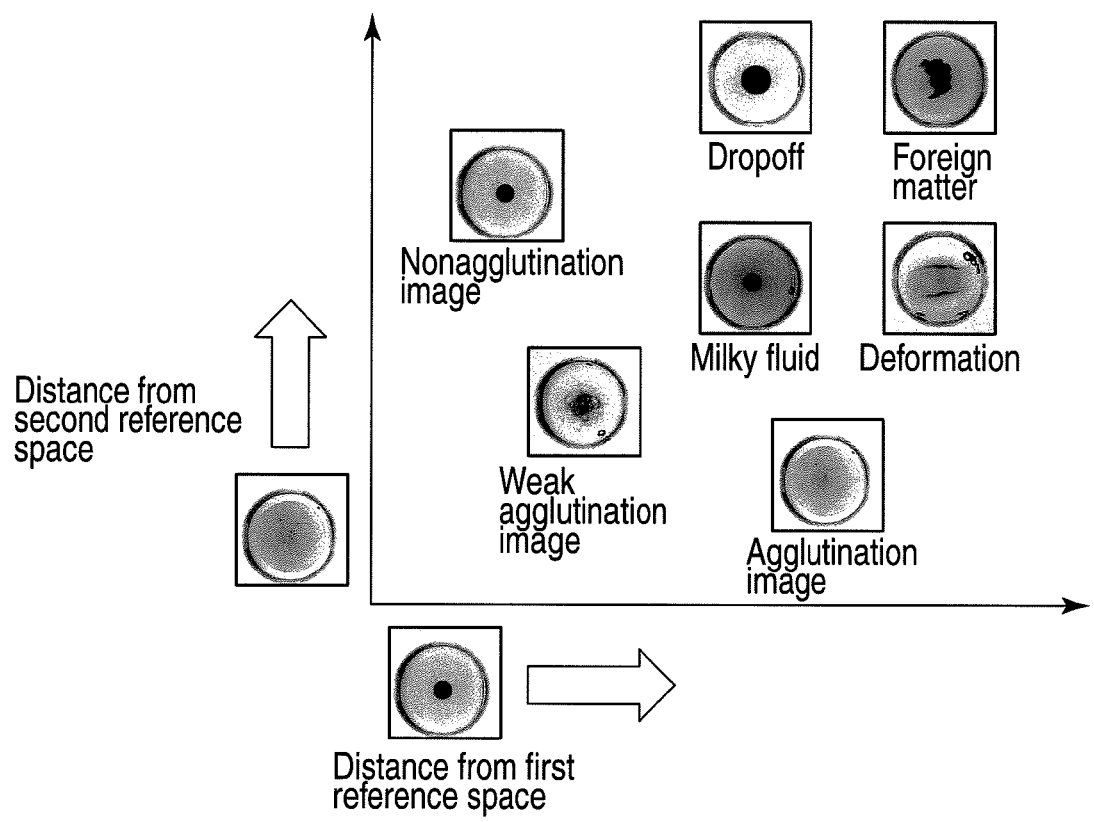
F I G. 24

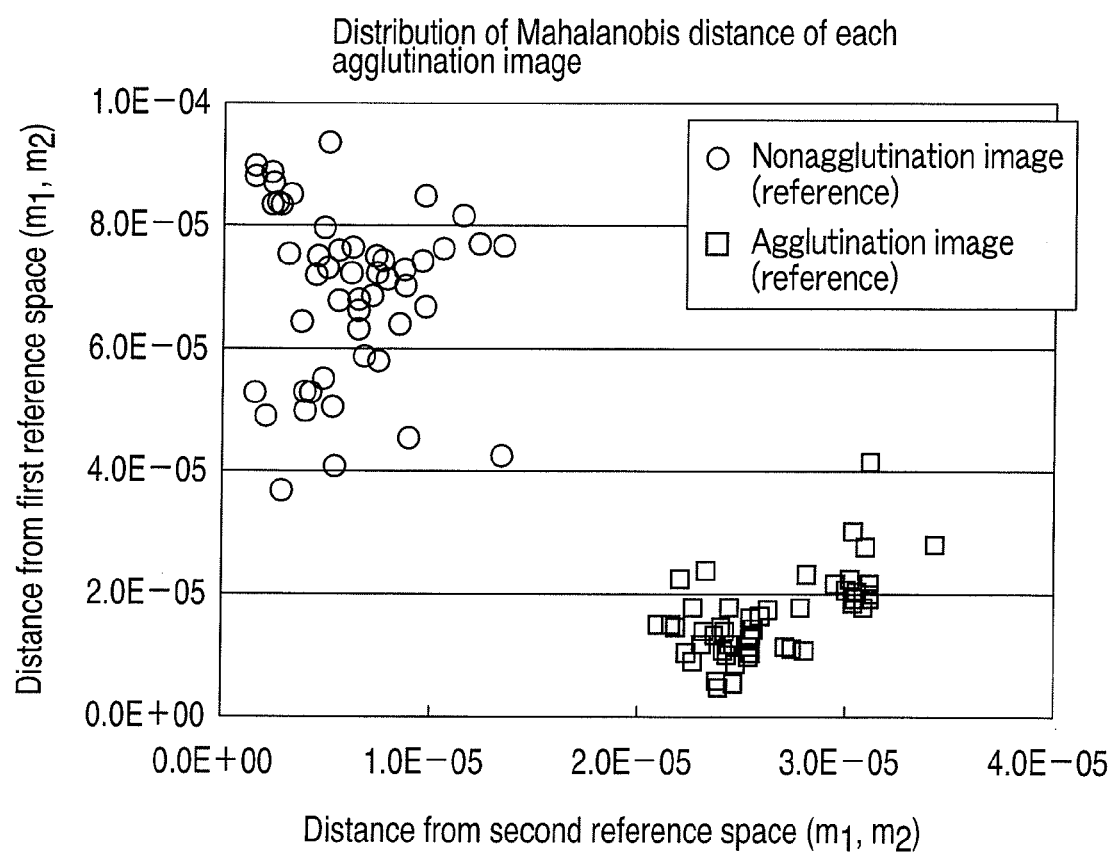
F I G. 25

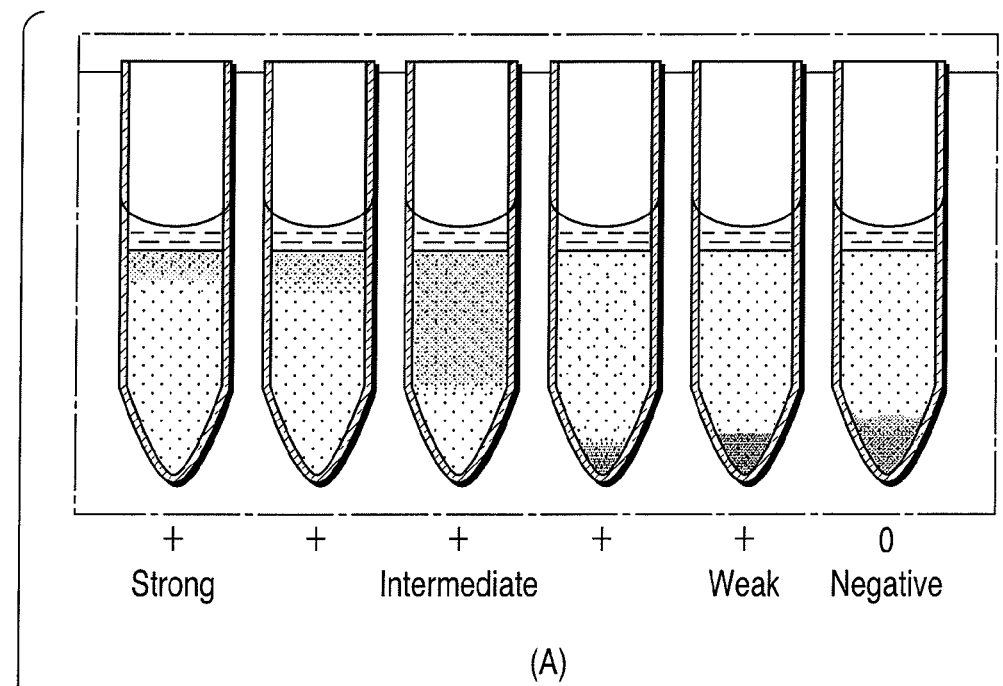
(A)
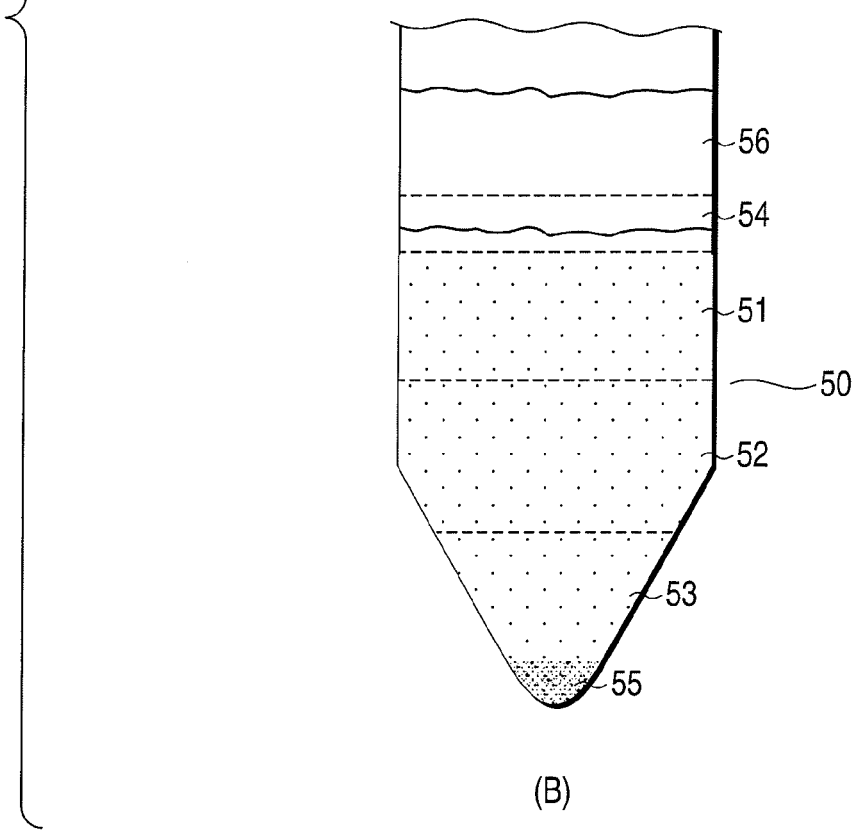
(B)
FIG. 29

AGGLUTINATION IMAGE AUTOMATIC JUDGING METHOD BY MT SYSTEM, DEVICE, PROGRAM, AND RECORDING MEDIUM

CROSS REFERENCE TO RELATED APPLICATIONS

This is a Continuation Application of PCT Application No. PCT/JP2008/061663, filed Jun. 26, 2008, which was published under PCT Article 21(2) in Japanese.

This application is based upon and claims the benefit of priority from prior Japanese Patent Application No. 2007-173149, filed Jun. 29, 2007, the entire contents of which are incorporated herein by reference.

BACKGROUND OF THE INVENTION

1. Field of the Invention

The present invention relates to a method and a system to automatically determine an agglutination image type.

2. Description of the Related Art

Background Art

According to a method currently available to determine a reaction image type formed by the agglutination reaction to inspect the blood group and infectious diseases, it is a common practice to determine the reaction image type automatically using an apparatus and then observe the reaction image with the naked eye to check that the automatic determination exhibits no problem. In the automatic determination, the agglutination image or the nonagglutination image is determined by the light amount change rate based on the overall contrast or the degree to which the boundary with a substance is blurred (Jpn. Pat. Appln. KOKAI Publication No. 4-72547).

Also, with the aim of approximating the automatic determination to the recognition by human being, a method has been proposed, as an example, in which a video image is processed and the agglutination image or the nonagglutination image is determined three-dimensionally based on the mean particle density and the accumulation amount in a certain concentration layer (Jpn. Pat. Appln. KOKAI Publication Nos. 9-145594 and 3-108638).

In these conventional automatic determination methods, the abnormality of the intended part is liable to be highlighted excessively. Even in the case where an agglutination image can be apparently observed as a whole, therefore, the proper determination may not be made.

Under the circumstances, therefore, a visual inspection is conducted on an image which cannot be determined accurately.

BRIEF SUMMARY OF THE INVENTION

The means of achieving the object above include the followings:

(1) A method of determining an agglutination pattern type for a pattern formed in a reaction vessel, comprising:
  (A) setting a plurality of reference spaces based on one or a plurality of types of typical reaction images;
  (B) setting one or a plurality of types of unit regions in each of the reference spaces obtained in (A) and determining a Mahalanobis distance for each unit region;
  (C) setting a threshold value from each of the Mahalanobis distances obtained in (B);
  (D) setting one or a plurality of unit regions for a reaction image to be determined as an object image and determining the Mahalanobis distance for each of the unit regions; and
  (E) determining the agglutination pattern type for the object image by comparing the threshold value set in (C) with the distances determined in (D):

(2) A method of determining an agglutination pattern type for a pattern formed in a reaction vessel, comprising:
  (A) setting a plurality of reference spaces based on one or a plurality of types of typical reaction images;
  (B) setting one or a plurality of unit regions for each of the reference spaces set in (A) and extracting a feature amount for each of the unit regions;
  (C) setting a threshold value by determining a Mahalanobis distance of a reaction image set in a reference space from the reference space based on each of the feature amounts obtained in (B);
  (D) setting one or a plurality of unit regions in the reaction images to be determined, and extracting the feature amount of each of the unit regions;
  (E) determining the Mahalanobis distance of each reaction image from the reference space based on the feature amount obtained in (D); and
  (F) determining the agglutination pattern type for the object image by comparing the threshold value set in (C) with the distance determined in (E):

(3) The method according to (1) or (2), wherein the steps (A) to (C) are executed in advance, and based on the setting thus obtained, the steps (D) to (F) are carried out repeatedly:

(4) The method according to any one of (1) to (3), wherein a plurality of unit regions are set in the (B) and at least two of said plurality of unit regions have different areas:

(5) The method according to any one of (1) to (4), wherein agglutination is determined based on a relation between the Mahalanobis distances of the intended reaction image determined from one or a plurality of regions in one or a plurality of reference spaces by comparing the threshold value and the distance with each other:

(6) The method according to any one of (1) to (4), wherein agglutination is determined based on the integrated Mahalanobis distance of the intended reaction image determined from one or a plurality of regions in one or a plurality of reference spaces by comparing the threshold value and the distance with each other:

(7) A method of determining an agglutination pattern type for a pattern formed in a reaction vessel, comprising:
  (a) selecting a nonagglutination image for a first reference space and an agglutination image for a second reference space;
  (b) setting a unit region for each of the image for the first reference space and the image for the second reference space, and extracting a statistical amount;
  (c) determining a Mahalanobis distance for the first reference space from the statistical amount of the unit region of the first reference space and a Mahalanobis distance for the second reference space from the statistical amount of the unit region of the second reference space;
  (d) setting a unit region for an object image and extracting the statistical amount for each unit region;
  (e) determining a distance of the object image from the first reference space and the second reference space based on the statistical amounts obtained in (d) and the Mahalanobis distance; and
  (f) determining the agglutination pattern type based on the distance obtained in (e):

(8) The method according to (7), wherein the steps (a) to (c) are executed in advance, and based on the distance obtained thereby, the steps (d) to (f) are repeatedly executed:
(9) The method according to (7) or (8), wherein the unit region comprises a first region:
(10) The method according to (7) or (8), wherein the unit region comprises a first region and a second region:
(11) The method according to (10), wherein the determination of (f) is effected based on the relation of the first region of the object image with the first region of the first reference space and the first region of the second reference space, and the relation of the second region of the object image with the second region of the first reference space and the second region of the second reference space:
(12) The method according to (10), wherein the determination of (f) is effected based on the relation of the integrated Mahalanobis distance of the first region of the first reference space and the first region of the second reference space with the first region of the object image, and the relation of the integrated Mahalanobis distance of the second region of the first reference space and the second region of the second reference space with the second region of the object image:
(13) The method according to any one of (1) to (12), wherein all the images are converted to a grayscale before being used:
(14) The method according to any one of (1) to (13), wherein the Mahalanobis distance is determined by selected one of an MTA method and an MT method using a brightness value of each pixel of the image:
(15) The method according to any one of (1) to (14), wherein the nonagglutination image is an image with particles collected at a center of the bottom surface of the reaction vessel, and the agglutination image is an image with the particles existing over the entire bottom surface of the reaction vessel:
(16) The method according to any one of (1) to (14), wherein the reaction vessel comprises a tubular portion, and the nonagglutination image is formed with the particles collected at the lowest part of the tubular portion and the agglutination image is formed with the particles collected in the upper part of the tubular portion:
(17) The method according to any one of (1) to (14), wherein one side of the reaction vessel is in solid phase to form a specific bonding pair therein:
(18) The method according to any one of (1) to (17), wherein the agglutination reaction is a blood agglutination reaction:
(19) The method according to any one of (1) to (18), wherein at least one of the unit regions is defined by selected one of a polygon and a circle of the reaction image containing the center of the reaction vessel:
(20) The method according to any one of (13) to (18), wherein the first region is defined by selected one of a polygon and a circle of the image inscribed in an inner wall of the vessel, and the second region is defined by selected one of a polygon and a circle concentric with selected one of the polygon and the circle of the first region:
(21) The method according to (20), wherein the first region and the second region are defined by shapes similar to each other:
(22) The method according to any one of (10) to (18), (20) and (21), wherein the first region and the second region have different areas:
(23) The method according to any one of (10) to (18) and (20) to (22), wherein the area of the first region is larger than that of the second region:

(24) An apparatus which automatically determines an agglutination pattern type for an object formed in a reaction vessel, comprising;
a data processing unit configured to make determination according to a criterion based on a Mahalanobis distance determined from a first reference space corresponding to at least one typical nonagglutination image and a second reference space corresponding to at least one typical agglutination image; and
an image acquisition unit configured to acquire a reaction image of the object to be transmitted to the data processing unit,
wherein the data processing unit determines the agglutination pattern type according to the computation result based on the Mahalanobis distance:
(25) The automatic determination apparatus according to (24), wherein the criterion has a plurality of stages of threshold values corresponding to the Mahalanobis distance for the first reference space and the second reference space, and based on each threshold value, the pattern of an intermediate agglutination between agglutination and nonagglutination is classified:
(26) The automatic determination apparatus according to (24) or (25), wherein the criterion has such a threshold value that a given agglutination far from the first reference space and near the second reference space is classified as agglutination, and a given agglutination near the first reference space and far from the second reference space is classified as nonagglutination:
(27) The automatic determination apparatus according to any one of (24) to (26), further comprising an input unit configured to set at least one of the number and the area of the unit region for calculating the Mahalanobis distance:
(28) The automatic determination apparatus according to any one of (24) to (26), further comprising a display unit configured to display an agglutination image group and a nonagglutination image group constituting candidates for the first and second reference spaces, and an input unit configured to designate at least selected one of an image and the number of images based on the image group displayed on the display unit:
(29) An agglutination pattern determination program which, in order to determine an agglutination pattern type for a pattern formed in a reaction vessel, causes a computer to function as;
a first data processing unit configured to make determination according to a stored criterion based on the Mahalanobis distances determined from a first reference space corresponding to at least one typical nonagglutination image and a second reference space corresponding to at least one typical agglutination image;
an image acquisition unit configured to acquire a reaction image of an object and transmit the acquired reaction image to the data processing unit;
a second data processing unit configured to compute the Mahalanobis distance based on the reaction image obtained by the image acquisition unit; and
a third data processing unit configured to determine the agglutination pattern type for the object by comparing the criterion with the Mahalanobis distance based on the reaction image:
(30) The program according to (29), wherein in order to classify an intermediate agglutination pattern between agglutination and nonagglutination, the stored criterion includes a plurality of stages of threshold values corresponding to the Mahalanobis distance to the first and second reference spaces:

(31) The program according to (29) or (30), wherein in order to determine the agglutination pattern type, the stored criterion includes a threshold value for classifying the agglutination pattern as an agglutination in the case where the distance is long from the first reference space and short from the second reference space, and classifying the agglutination pattern as a nonagglutination in the case where the distance is short from the first reference space and long from the second reference space:

(32) The program according to any one of (29) to (31), wherein the computer further functions as an input unit configured to set at least one of the number and the area of the unit regions for calculating the Mahalanobis distance:

(33) The program according to (29),
wherein the computer is caused to function further as:
a display unit configured to display an image group of agglutination and nonagglutination as candidates for the first and second reference spaces; and
an input unit configured to designate at least one of an image and the number of images based on the image group displayed on the display unit: and

(34) A computer readable recording medium having recorded therein the program according to any one of (29) to (33) in a way readable by the computer.

The advantages of the invention are illustrated in and partly made apparent by the description that follows, or can be learned by embodying the invention. The advantages of the invention can be understood and obtained from the drawings and the combination thereof with the specific description later.

BRIEF DESCRIPTION OF THE SEVERAL VIEWS OF THE DRAWING

FIG. 1 is a diagram showing the concept of a method according to the invention.

FIG. 3 is a diagram showing typical nonagglutination and agglutination images acquired by a CCD camera.

FIG. 4 is a diagram showing a typical abnormal image captured by the CCD camera.

FIG. 9 is a diagram showing equations used in the method according to the invention.

FIG. 10 is a diagram showing the intuitive meaning of the elements in the equations used in the method according to the invention.

FIG. 11 is a diagram showing an example of a table generated according to the invention.

FIG. 12 is a diagram showing an example of a table generated according to the invention.

FIG. 14 is a diagram showing an example of the data processing operation used in the method according to the invention.

FIG. 15 is a diagram showing an example of a table generated according to the invention.

FIG. 16 is a diagram showing the equations used in the method according to the invention.

FIG. 17 is a diagram showing the equations used in the method according to the invention.

FIG. 18 is a flowchart for explaining step S5B of FIG. 5 further.

FIG. 19 is a diagram showing an example of a table generated according to the invention.

FIG. 20 is a diagram showing the equations used in the method according to the invention.

FIG. 21 is a diagram showing an example of devices used in the invention.

FIG. 23 is a diagram showing an example of tables generated in the invention.

FIG. 24 is a diagram showing an example of a graph generated according to the invention.

FIG. 25 is a diagram showing an example of a graph generated according to the invention.

FIG. 29 is a diagram showing one aspect of the invention.

DETAILED DESCRIPTION OF THE INVENTION

Figure 2:
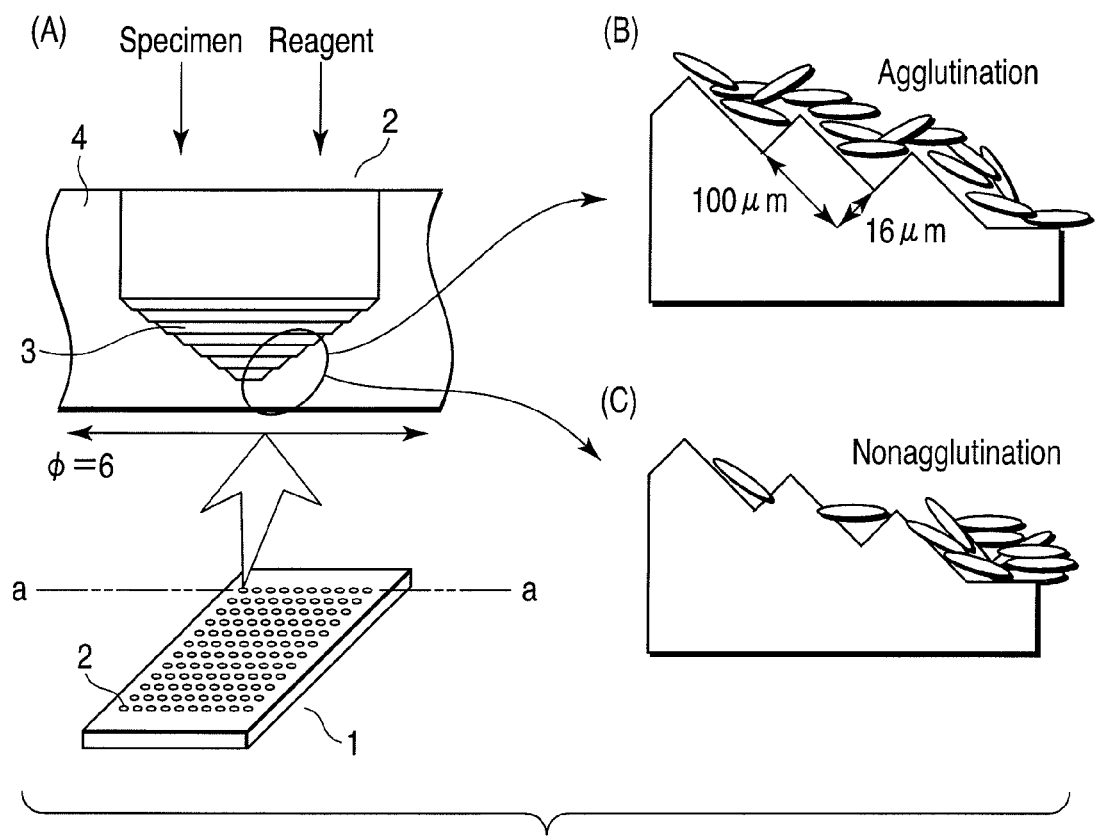
FIG. 2 is a diagram showing an example of a reaction vessel used in the invention and a pattern formed therein.

In this method, the agglutination pattern is considered to have two types of reference spaces, i.e., a first reference space obtained from the nonagglutination image and a second reference space obtained from the agglutination image.

According to the invention, the feature amount is determined from each of the first and second reference spaces obtained from the nonagglutination image using the MT system, and the Mahalanobis distance is calculated from the feature amounts. With regard to an object image constituting a reaction image of an object, on the other hand, the feature amount is also determined like the reference space using the MT system, and based on this feature amount, the relation between the Mahalanobis distances from the first and second reference spaces is determined by comparison, thereby making it possible to determine whether the object image is associated with the pattern of nonagglutination or agglutination or neither of the patterns.

Refer to FIG. 1. FIG. 1 shows the concept of the method according to the invention. In the case where the Mahalanobis distance of the object image is short (near) from the first reference space and long (far) from the second reference space, the pattern is determined as nonagglutination. In the case where the Mahalanobis distance of the object image is long from the first reference space and short from the second reference space, on the other hand, the pattern is determined as agglutination. Also, in the case where the Mahalanobis distance of the object image is short or long from both the first and second reference spaces, the determination is made as "indeterminate".

The MT system according to the invention, which may be of any type, is preferably the MTA method or the MT method, or especially, the T method (i.e., the RS method or the RT method) using a reference signal-to-noise (SN) ratio. An example of the MT system and an example of the T method using the reference signal-to-noise ratio applicable to the invention are described in detail in "Genichi Taguchi: T Method Using Image Recognition and Reference SN Ratio", Standardization and Quality Control, Vol. 58, No. 11 and "Kazuhito Takahashi: Identification of Reference SN Ratio of Handwritten Characters by T Method", Collected Papers at 14th Quality Optical Research Presentation Conference, Quality Engineering Society.

The term "specimen" used herein may be the one containing an antigen, an antibody or one of the substances of a bond pair generating a specific bond adapted to cause the agglutination reaction, or preferably, blood. The term "reagent" used herein, on the other hand, may be the one containing a substance generating an agglutinate specifically by the reaction with an antigen, an antibody or one of the substances making up the bond pair, or for example, an antigen, an antibody or the other substance of the bond pair. An example of a substance capable of forming a specific agglutinate other than the specific bonding by an antigen or an antibody includes a nucleic acid complementary pairing exhibiting what is called the hybridization reaction.

The agglutination pattern used in the invention may be formed in any reaction vessel generally used for the agglutination reaction. Also, the image used in the determination method according to the invention is preferably the one obtainable by an imaging unit from an agglutination pattern formed in the reaction vessel.

Based on the feature of the pattern formed in the reaction vessel in this way, the result of reaction between the specimen and the reagent can be classified and/or determined.

The reaction vessel used in the invention is not limited to the aforementioned one, and may be any vessel well known to those skilled in the art, such as a vessel generally used for the agglutination test. Some examples of such a vessel include a microplate having a flat, U-shaped and/or V-shaped bottom surface, various test tubes, a reaction vessel having a terrace slope as disclosed in Japanese Patent No. 3629023, or a cassette-type vessel as disclosed in Jpn. Pat. Appln. KOKOKU Publication No. 8-7215 or Jpn. Pat. Appln. KOKAI Publication No. 11-101797. Further, a slide glass may be used as a reaction vessel.

Also, inside such a vessel or, for example, on the bottom surface of the vessel, the desired antigen such as red blood cells, white blood cells or blood platelets in solid phase exists in a gel such as glass or latex. The method of fabricating such a vessel is well known to those skilled in the art.

According to the invention, the agglutination reaction inspection is conducted using the aforementioned vessel by the agglutination test methods well known to those skilled in the art, as disclosed in Jpn. Pat. Appln. KOKOKU Publication No. 8-7215 or Jpn. Pat. Appln. KOKAI Publication No. 11-101797, which include the static agglutination method, the centrifugal agglutination method, the plate solid phase method, the mixed passive hemagglutination method (generally called "MPHA") or the column agglutination method using the gel or beads. Specifically, the agglutination test according to the invention may be any one including the blood group test or the antigen antibody reaction for detecting an infectious disease utilizing the agglutination reaction. Also, any test method may be used which results in the existence of the agglutination image and the nonagglutination image.

The term "reference space" used in the invention has been described above as a typical "agglutination image" and a typical "nonagglutination image". Nevertheless, the reference space according to the invention is not limited to such images, but two types of reaction images including "the intermediate agglutination image" and/or "the intermediate nonagglutination image" may be set as a reference space. Also, an arbitrary "abnormal image" may be selected appropriately as a reference space. This is desirable in view of the fact that an abnormal image can be discriminated with high accuracy. Thus, the reference space can be selected as desired by the inspector. For example, "the agglutination image", "the nonagglutination image", "the intermediate agglutination image", "the intermediate nonagglutination image" and/or an arbitrary "abnormal image" may be combined as desired or a single reference space may be selected by the inspector.

The term "unit region" in the invention may be any region for obtaining the feature amount. One or plural unit regions may be set for a problem image. For example, two, three, four or more plural unit regions may be set and used. The "unit region" is hereinafter sometimes referred to simply as "the region".

An example of the reaction vessel having the terrace slope is shown in FIGS. 2A and 2B, to which the invention is not limited. The reaction vessel shown in FIG. 2A is a microplate 1, and the actual reaction occurs in wells 2 thereof. The upper diagram in FIG. 2A is a sectional view 4 of one well with the microplate 1 cut off along line a-a. A terrace 3 is formed on the bottom surface of the well 2. In this vessel, as shown in FIGS. 2C and 3A, the cells not agglutinated slide down the slope of the terrace 3 and are collected at the lowest portion of the bottom surface of the reaction vessel, i.e., at the center of the bottom surface of the well of the vessel. As a result, a typical nonagglutination image as shown in FIG. 3A is obtained. The agglutinates formed by the reaction, on the other hand, as shown in FIG. 2B, are caught by the terrace 3 and spread uniformly over the entire bottom surface. As a result, a typical agglutination image as shown in FIG. 3B is obtained. Thus, FIG. 3A shows a typical nonagglutination image; and FIG. 3B, a typical agglutination image. In the case where another method such as the centrifugal agglutination method is used, on the other hand, an agglutinate mass is collected at the center of the bottom surface of each well, while in the case of nonagglutination, an image is obtained with the particles separated and distributed over the whole bottom surface of the well. This invention is applicable also to such other methods with equal effect.

The image formed on the bottom surface of the reaction vessel after the agglutination reaction, if neither the agglutination image nor the nonagglutination image, is an abnormal image or a weak agglutination image, for example. Such an image may be determined as "indeterminate". Examples of abnormal images are shown in FIG. 4.

FIG. 4A shows an abnormal image of what is called "dropoff"; FIG. 4B, what is called "milky fluid"; FIG. 4C, what is called "deformation"; and FIG. 4D, what is called "foreign matter". In the case where the object image to be determined is any of these abnormal images, the determination "reinspect" or "indeterminate" is required. In the method according to the invention, these abnormal images can also be appropriately determined in accordance with the type thereof.

2. Determination Method

Figure 5:
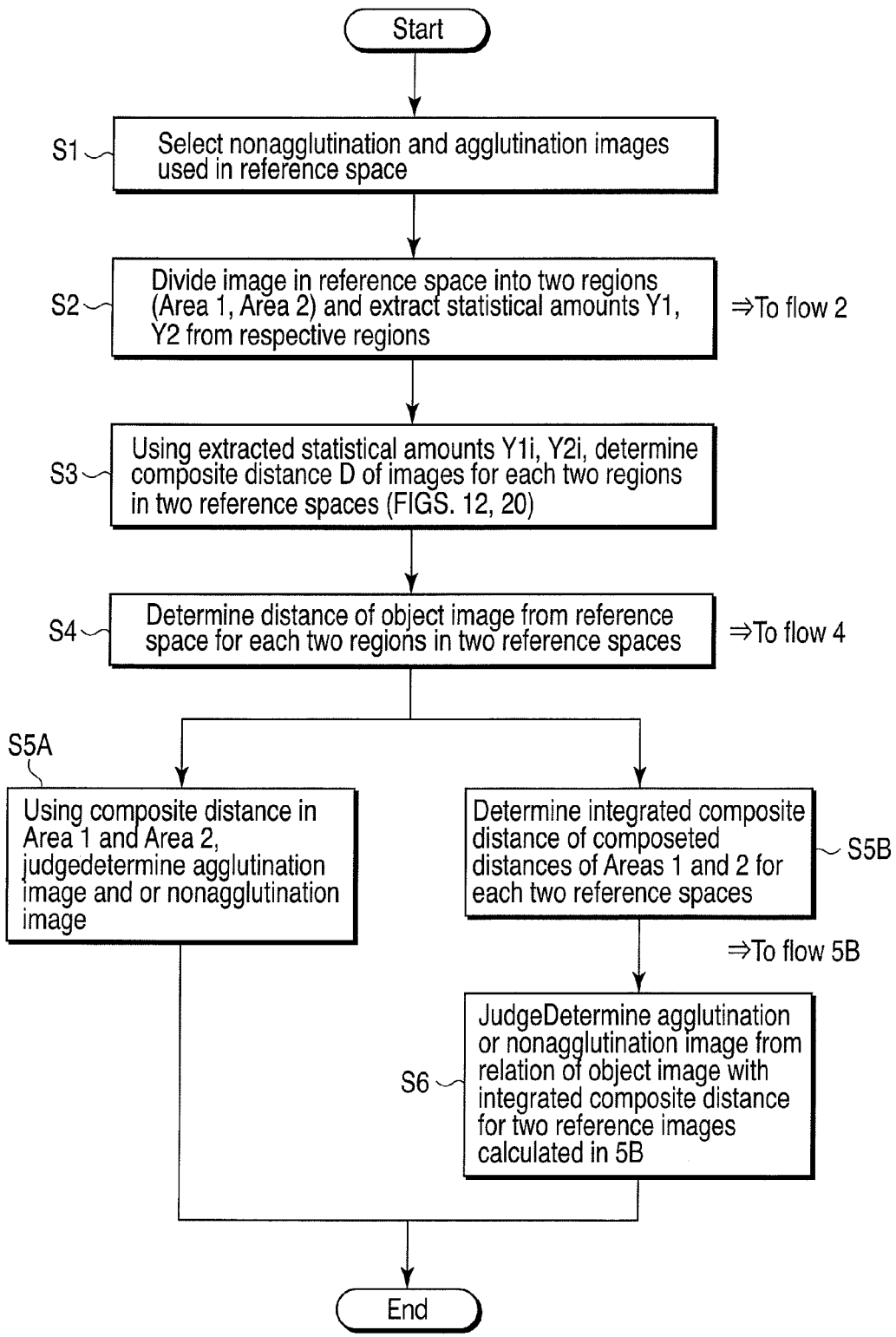
FIG. 5 is a flowchart showing a method according to one aspect of the invention.

An example of determination made for an agglutination image according to the invention is explained with reference to the scheme shown in FIG. 5. Refer to FIG. 5.

After the agglutination reaction, the method starts to be carried out for determining whether an image containing the pattern formed on the bottom surface of the reaction vessel is an agglutination image or a nonagglutination image. First, the process proceeds to step S1.

In step S1, a typical image for generating reference data to determine an object is selected. Specifically, in order to generate a first reference space from the nonagglutination image and a second reference space from the agglutination image, typical nonagglutination and agglutination images are selected.

The images to be selected may be captured by the imaging unit for each determination session, or may be selected from the images captured in advance. As another alternative, such images may be acquired from any database available.

If required in the process, the reference space of the nonagglutination image may be obtained by adjusting the typical nonagglutination image captured in advance to a predetermined size. In similar fashion, if required, the agglutination image for the reference space may be obtained by adjusting the typical agglutination image captured in advance to a predetermined size. Also, before or after or in the absence of the size adjustment, each image may be converted to a grayscale. The grayscale may have 256 gradations, for example.

The number of the images used in this case can be determined arbitrarily as desired by the inspector.

Mathematically, however, the number of images may satisfy the relation "feature amount≧number of images" in the MT method. According to the MTA method, the number of the image may be single or, for practical purposes, may be not less than three or preferably not less than 50.

The nonagglutination image may be a typical one that can be determined so by those skilled in the art. In the case where the well comprising the terrace described above is used, the image may be the one in which the agglutinates exist at the center of the bottom surface thereof, for example, as shown in FIG. 3A.

The agglutination image, on the other hand, may be a typical one that can be determined so by those skilled in the art. In the case where the well comprising the terrace described above is used, the image may be the one in which the agglutinates exist uniformly over the entire bottom surface as shown in FIG. 3B. Even the visual determination by human being, however, is accompanied by a variation from one image to another. As a typical image, therefore, it is desirable to select a representative image containing such variation in order to make it possible to reflect the effect of the variation in the range determinable by human being. Taking the inclusion of such a representative image into consideration, at least 50 each of the nonagglutination images and the agglutination images are preferably used.

After selecting at least the required number of images in step S1, the process proceeds to step S2.

Figure 6:
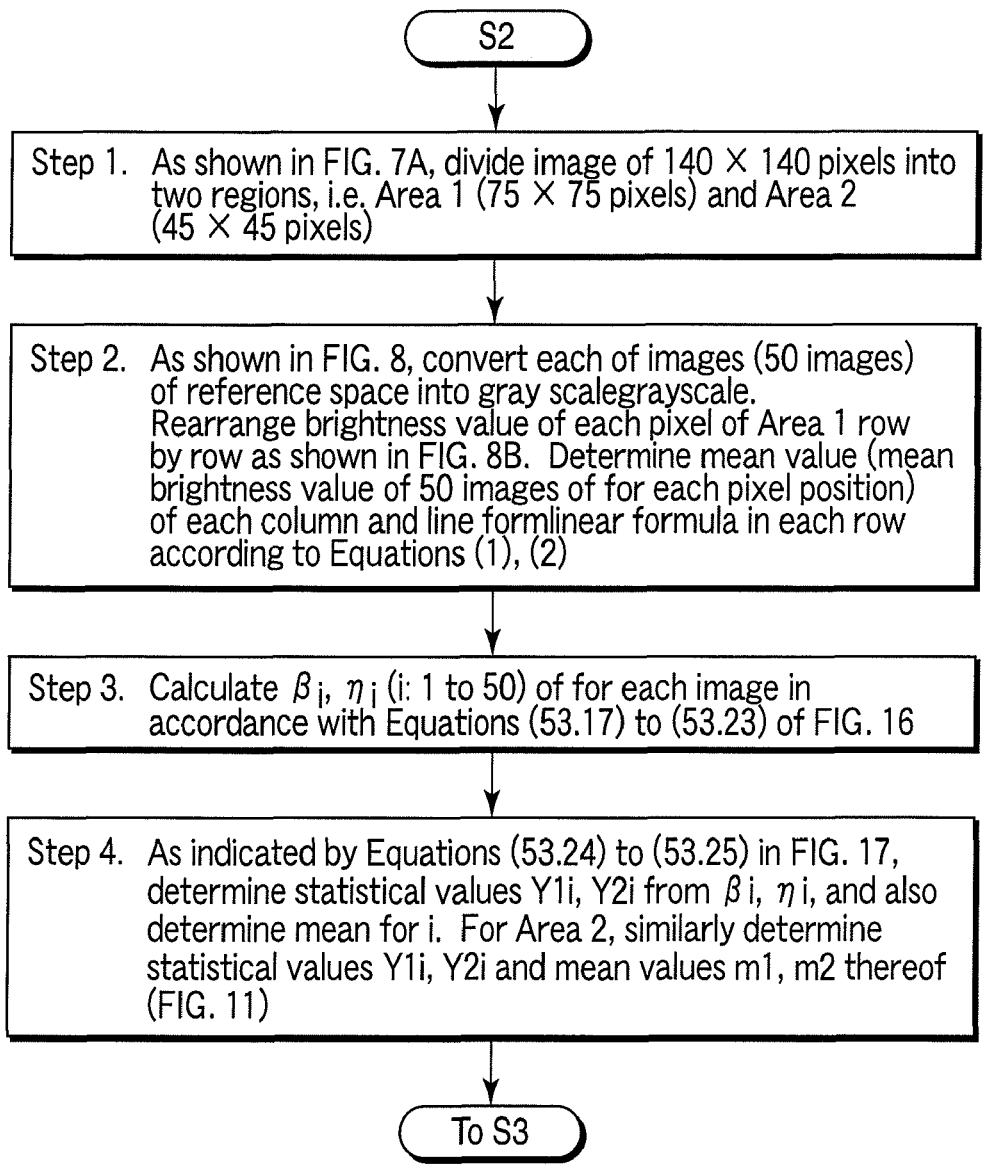
FIG. 6 is a flowchart for explaining step S2 in FIG. 5 further.

In step S2, the images selected in step S1, i.e., all the predetermined number of plural nonagglutination and agglutination images are each divided into two regions, and for each region, the statistical amount is extracted and the process proceeds to step S3. Step S2, for example, may be as shown in the flow 2 in FIG. 6.

Figure 7:
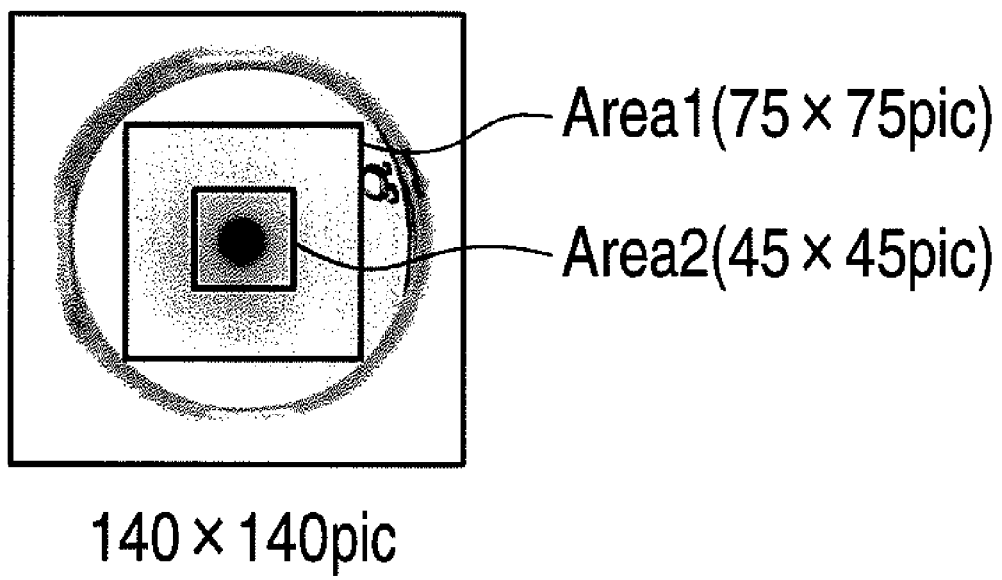
FIG. 7 is a diagram showing an example of a region used in the invention.

In step 1 of the flow 2, the image is divided into two regions. In the case where the number of pixels per image is 140×140, for example, the first region (also referred to as "Area 1" in this specification and the accompanying drawings) making up a unit region may be, for example, 75×75 pixels, while the second region (also referred to as "Area 2" in this specification and the accompanying drawings) making up a unit region may be, for example, 45×45 pixels. Refer to FIG. 7. The image shown in FIG. 7 is a nonagglutination image formed on the bottom surface of the reaction vessel comprising the terrace. In the case where the region described above is divided into two regions, for example, the first region preferably includes the entire part of the bottom surface over which the agglutinates of the agglutination image are distributed, and preferably is inscribed in the bottom surface of the reaction vessel. The second region, on the other hand, preferably includes the neighborhood of the center at which the nonagglutinates of the nonagglutination image are collected, and preferably arranged on the inside of the first region.

Although an example in which two regions are each used as a unit region has been described above, the method of the invention is not limited to two regions, nor the configuration of the first and second regions limited to the one described above. In the case where plural regions are used as unit regions, for example, they may or may not be superposed on another region. In any case, the size of each region may or may not be the same or different.

For example, the first region may be a rectangle inscribed in the image of the well, and the second region may be in the shape similar to, concentric with and smaller in region than the first region. Such a region, however, may not be a rectangle but a circle or a polygon. Further, the first and second regions are not necessarily similar to each other.

In the example described above, both the first and second regions include that portion of the typical agglutination image or the typical nonagglutination image at which particles are most concentrated, and the first and second regions have different areas.

The determination method according to the invention may be used in a test for classifying the reaction result and/or an agglutination test for determining the agglutination or nonagglutination based on the features of the pattern formed on the bottom surface of the reaction vessel after reaction between the specimen and the reagent.

Further, the statistical amount is extracted as a feature amount of the first and second regions. The statistical amount is calculated based on the brightness value of each pixel included in each image. After executing this process, the control is passed to step 2.

In step 2, each image may be converted to a grayscale for the first time. An example is explained here in which 50 nonagglutination images and 50 agglutination images are used. The brightness value of each pixel included in the first region of one image converted to the grayscale is rearranged as shown in FIG. 8B. Similarly, the brightness value of each pixel included in the second region is rearranged. By repeating this process, a similar result is obtained for all the images. After that, as shown in FIG. 8C, a table is generated in which the pixel position and the image number are shown in correspondence with each other. The term "mean" in FIG. 8C indicates the mean value, which is calculated according to Equation (1) shown in FIG. 9. The linear formula is calculated according to Equation (2) shown in FIG. 9. After executing this process, the control is passed to step 3.

In step 3, the difference of each member with the mean (i.e., $M_1, M_2, \ldots, M_{5625}$) of all the pixels at the same position included in one region of the reference space is determined based on a proportionality constant $\beta i$ and a signal-to-noise ratio $\eta i$ (i: integer of 1 to 50), where $\beta i$ and $\eta i$ are calculated from Equations (53.17) to (53.23) shown in FIG. 16. In these equations, the intuitive meaning of $S_T(i)$, $S_\beta(i)$ and $V(i)$ is shown in FIG. 10. After calculating $\beta i$ and $\eta i$, the process proceeds to step 4.

In step 4, the statistical amounts $Y_{1i}$ and $Y_{2i}$ of the first region of each image are determined based on the values $\beta i$ and $\eta i$ obtained in step 3. These statistical amounts can be determined according to Equations (53.24) to (53.25) shown in FIG. 17. Further, the mean (i.e., $m_1$) of the statistical amounts of the first region of the first reference space is determined from the statistical amounts obtained for all the images as shown in FIG. 11. After making the calculations for all the regions including the first region of the first reference space, the second region of the first reference space, the first region of the second reference space and the second region of the second reference space in steps 3 and 4, the process proceeds to step S3 (FIG. 5).

In step S3, the composite distance, i.e., the Mahalanobis distance is determined for each of the first and second regions in the two reference spaces, i.e., the first and second reference spaces using the statistical amounts $Y_{1i}$ and $Y_{2i}$ extracted (i.e., calculated) in step S2. Specifically, as shown in FIG. 12, the Mahalanobis distances ($D_i$) can be obtained from Equations (53.28), (53.29), (53.30) and (53.31). In FIG. 12, the four composite distances of the image used in the reference space are calculated according to Equations (53.28) to (53.31) for each of the two regions (Area 1 and Area 2) of the two reference spaces (nonagglutination image and agglutination image). After that, the process proceeds to step S4.

The steps described above, i.e., step S1, steps S1 and S2 or steps S1 to S3 may be executed before conducting the agglutination test and/or determining the agglutination. Also, the data thus obtained may be stored in an arbitrary storage unit and accessed or used as desired. In this way, by executing step S1, steps S1 and S2 or steps S1 to S3 in advance, the inspector can start the agglutination determination after step S1, steps S1 and S2 or steps S1 to S3, respectively. The method carried out with this configuration is also defined as the agglutination determination method within the scope of the invention.

In step S4, the distance of the image desired for determination, i.e., the object image from the reference space is determined using the Mahalanobis distance of the reference space obtained in step S3. Then, the process proceeds to flow 4.

Figure 13:
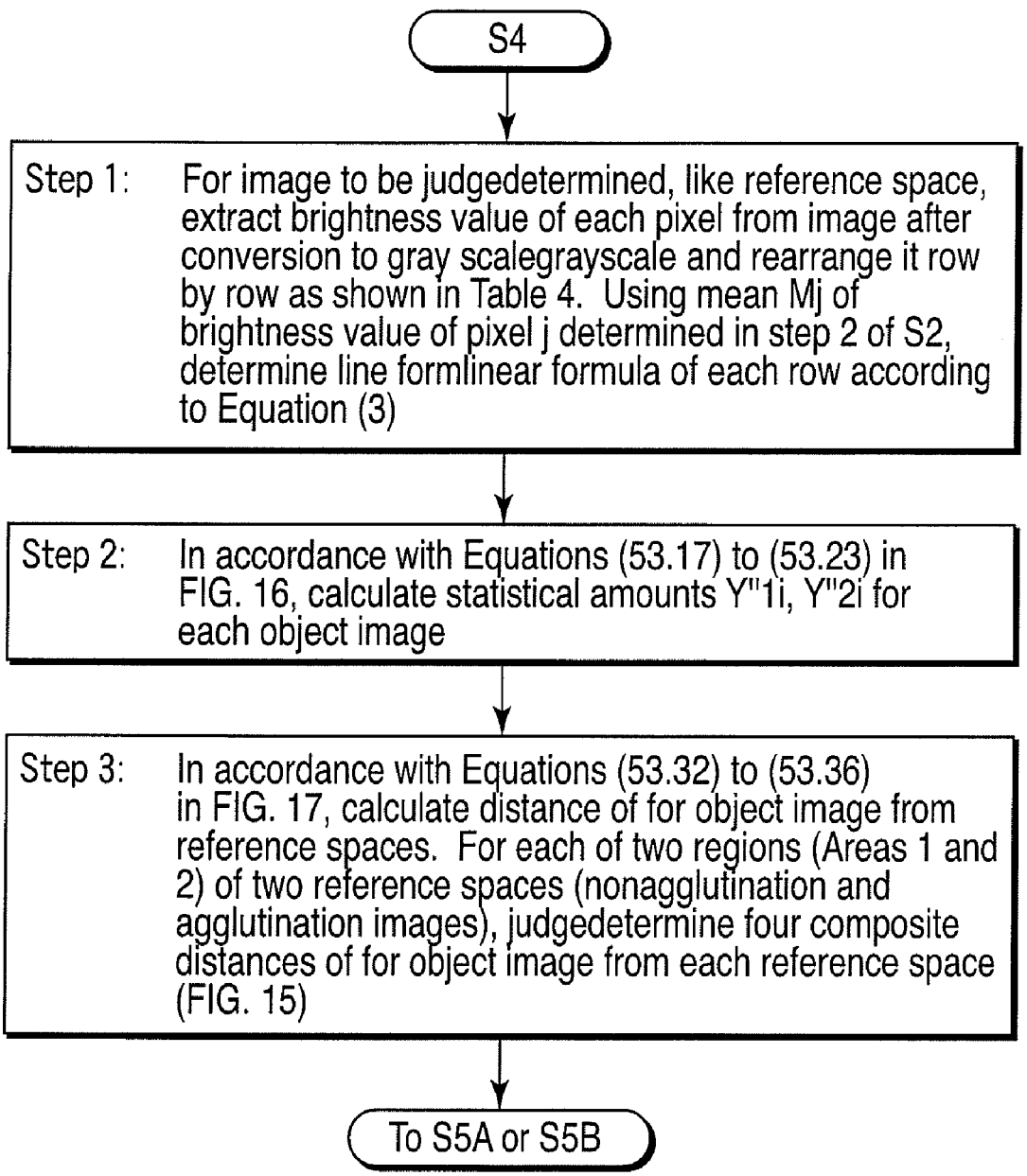
FIG. 13 is a flowchart for explaining step S4 of FIG. 5 further.

Flow 4 is shown in FIG. 13. In step 1 of flow 4, a process similar to the one executed for the object image in the reference space is executed thereby to extract the brightness value of each pixel. Further, the numerical values thus obtained, like those for the data of the reference space, may be summarized in a table as shown in FIG. 14A, where the value $L'_k$ may be obtained from Equation (3) shown in FIG. 14B. Next, the process proceeds to step 2 of flow 4 (FIG. 13).

In step 2, the statistical amount for each object image is calculated. The statistical values are $Y'_{1i}$ and $Y'_{2i}$, which may be calculated according to Equations (53.17) to (53.23) shown in FIG. 16. Next, the process proceeds to step 3 (FIG. 13).

In step 3, the distance D' of the object image from the reference space is calculated. This calculation can be made according to Equations (53.31) to (53.36) shown in FIG. 20. Using these equations, four distances are determined for each two regions (i.e., the first and second regions) of the two reference spaces (i.e., the nonagglutination image and the agglutination image), i.e., for each image intended for determination. The distances thus determined can be summarized in a table as shown in FIG. 15. After that, the process proceeds to step S5A or S5B (FIG. 5) as appropriately selected by the inspector. In spite of this, a similar satisfactory result can be obtained by either the process of step S5A or the process including S5B and the next step S6.

In step S5A, the agglutination image or the nonagglutination image is determined based on the distance of each of the first and second regions of the object image from the reference space. This determination may be made alternatively by first determining a threshold value or a reference value and comparing the particular value with the distance.

For example, this determination is made as:
(1) "a nonagglutination image" in the case where the object image is near the nonagglutination image and far from the agglutination image,
(2) "an agglutination image" in the case where the object image is near the agglutination image and far from the nonagglutination image, and
(3) "neither an agglutination image nor a nonagglutination image", "indeterminate" or "?" in the case where the object image is far from both the nonagglutination image and the agglutination image.

As an alternative, the determination is made as:
(1) "a nonagglutination image" in the case where the object image is a nonagglutination image in both the first and second regions,
(2) "an agglutination image" in the case where the object image is an agglutination image in both the first and second regions, and
(3) "neither an agglutination image nor a nonagglutination image", "indeterminate" or "?" in the other cases.

The determination as to whether the object image is "far" or "near" may be made by comparing the distance with a predetermined threshold value or reference value. After the determination, the process proceeds to the end, thereby finishing the entire process.

In step S5B, another Mahalanobis distance as an integration of the Mahalanobis distances for the first and second regions is determined for the first and second reference spaces. Specifically, the process proceeds to flow 5B (FIG. 18).

Flow 5B is shown in FIG. 18. In step 1 of flow 5B, the mean value of the Mahalanobis distance $D_1$ of the first region and the Mahalanobis distance $D_2$ of the second region is determined for each image of the reference space. In FIG. 18, a mean of a certain group of numerical values is indicated by attaching a solid line above (or a slash before) the character indicating the particular group of numerical values. For example, the mean value of $D_1$ is indicated by attaching a solid line above (or a slash before) $D_1$. Next, the process proceeds to step 2.

In step 2, the mean of the Mahalanobis distance $D_i$ for the first region and the mean of the Mahalanobis distance $D_2$ for the second region are rewritten as $m_1$ and $m_2$, respectively, and so are $D_i$, $D_2$, $D_{ii}$, $D_{i2}$ rewritten as $Y_1$, $Y_2$, $Y'_1$, $Y'_2$, respectively. Then, the distance of the object image from the reference space is obtained using the integrated Mahalanobis distance for the first and second regions as calculated from Equations (53.28) to (53.31) shown in FIG. 20. Next, the process proceeds to step S6 (FIG. 5).

In step S6, the determination is made as "a nonagglutination image", "an agglutination image", "neither a nonagglutination image nor an agglutination image, "indeterminate" or "?" based on the distance of the object image from the reference space obtained in step S5B. This determination is made for the particular distance based on the threshold value or the reference value determined in advance. Also, the Mahalanobis distances of the first and second reference spaces are expressed in a two-dimensional distribution, based on which the determination may be made. Examples of the two-dimensional distribution are shown in FIGS. 25 to 28. The ordinate represents the Mahalanobis distance from the first reference space ($m_1$, $m_2$), i.e., the center or zero point thereof, and the abscissa the Mahalanobis distance from the second reference space ($m_1$, $m_2$), i.e., the center or zero point thereof. The relation between this distribution and the type of image is roughly shown in the model graph of FIG. 24. A threshold value or a reference value is determined in advance for the area having this distribution, and the determination may be made by comparing the value thereof. As described above, the determination is made as "a nonagglutination image", "an agglutination image", "neither a nonagglutination nor an agglutination, "indeterminate" or "?". After this determination, the process proceeds to the end to finish the entire process.

Also, the method according to the invention may be automatically implemented with a reaction device, an analysis device or an inspection device comprising a computer. The automatic blood transfusion inspection device PK series such as Automatic Blood Transfusion Inspection Device PK7300 of Olympus is an example to be used for such application.

Further, according to the invention, there may be provided, for example, an automatic agglutination image determination apparatus as shown in FIG. 21A. The automatic agglutination image determination apparatus shown in FIG. 21A comprises an illumination unit for radiating a light spot from the bottom surface through a lens group 33 by a light source 32 with the microplate 1 connected to a power supply 31, and a photodetector 34 for receiving the light beam radiated by the illumination unit and transmitted from the bottom surface of the well. The output of the photodetector 34 is converted to a digital signal by a received light data processing unit 35 and supplied to a data processing unit 36. Also, the microplate 1 is moved through a microplate transport mechanism 37 under the control of the data processing unit 36 thereby to produce scan data, while at the same time reconstructing the reaction image from the scan data by the received light data processing unit 35. The illumination unit, the photodetector 34, the received light data processing unit 35 and the microplate transport mechanism 37 provide a function as an image acquisition unit. In FIG. 21A, the image acquisition unit is defined by dotted line.

The data processing operation performed by the data processing unit 36 is explained below.

In the data processing unit 36, the data on the light received after scanning the bottom surface of the well 2 is converted to digital data as predetermined, and based on this data, an image is constructed and stored in the data processing unit 36. Further, in accordance with a command input from an input unit 38, the image is displayed on a display unit 39. Next, in accordance with a programmed procedure input from the input unit 38 and stored in the data processing unit 36 in advance, and further, by utilizing the data stored in the data processing unit 36, the data processing unit 36 makes the aforementioned calculation on the data for each pixel of the image data. The result obtained by this calculation is compared with the reference value input from the input unit and stored in the data processing unit 36 in advance thereby to make the determination as intended. The image used as a reference space may be either the data which is obtained by the apparatus in advance and stored accumulatively in the data processing unit 36 or the data input from the input unit 38 and stored in the data processing unit 36 in advance. Also, the required data may be acquired by connecting the data processing unit 36 to a network and by accessing a database available.

Also, according to the invention, there may be provided an automatic agglutination image determination apparatus as shown in FIG. 21B. The automatic agglutination image determination apparatus shown in FIG. 21B uses the microplate 1 as a reaction vessel which is illuminated uniformly from the bottom surface side thereof by an arbitrary illumination unit such as a fluorescent lamp 43 connected to a fluorescent light power supply 42 or the like power supply. The microplate 1, as shown in FIG. 2, is configured of a matrix of a great number of wells 2 each comprising a conically depressed bottom. Each well 2 has a detector of specimen particles to form a reaction pattern on the bottom surface according to the static method.

The images of the bottom surfaces of the wells 2 of the microplate 1 illuminated by the fluorescent lamp 43 are captured sequentially or at a time by an imaging unit 45 such as a video camera or a CCD camera. The illumination unit and the imaging unit 45 combine to function as an image acquisition unit. The image acquisition unit is defined by dotted line in FIG. 21B. The image data captured by the imaging unit 45 is supplied to an image processing circuit 46 and processed as desired. Further, a data processing unit 49 determines the brightness value of each pixel of the image data on the bottom surface of the wells 2 based on the input image data. Incidentally, the image data on the bottom surface of each well 2 may be retrieved sequentially by moving the microplate 1 and the imaging unit 45 relatively to each other two-dimensionally in a horizontal plane.

Now, the flow of the process executed in this apparatus is explained. The image obtained by the imaging unit 45 is sent to the image processing circuit 46. The image processing circuit 46 first converts the input image data of the bottom surface of the wells 2 supplied by the imaging unit 45 into digital data. Next, the brightness value for each pixel of the digital image data thus obtained is determined, and stored in the data processing unit 49 while at the same time displaying it on the display unit 41 in response to a command from the input unit 40. Next, in accordance with the preprogrammed procedure input from the input unit 40 and stored in the data processing unit 49, and further by using the data stored in the data processing unit 49, the calculations described above are made by the data processing unit 49 based on the image data for each pixel. The result obtained by the calculations are compared with the threshold value input from the input unit and stored in the data processing unit 49 in advance. In this way, the determination is made as intended. Also, the image to be used for the reference space may be either the data obtained by the apparatus and stored accumulatively in the data processing unit 49 in advance or the data input from the input unit 40 and stored in the data processing unit 49. As another alternative, by connecting the data processing unit 49 to a network, the required data may be acquired by accessing an available database.

This input unit 40 may be used, if required, as a unit as described later for selecting the image corresponding to each reference space, changing the number and/or the numerical value of the threshold or changing (i.e., increasing or decreasing) the set number of the unit regions. These operations of the input unit 40 are preferably confirmed through a setting screen adapted to be operated by the user or the inspector while watching the display unit 41. Specifically, the input unit 40 can be used as an input unit for setting the number and/or the size of the unit regions to calculate the Mahalanobis distance. Also, the display unit 41 can be used as a display unit for displaying the groups of agglutination and nonagglutination images as candidates for each reference space. The input unit 40 can be used for designating the image and/or the number of images based on the image group displayed on the display unit 41. Also, the input unit 40 can be used for setting the number and/or the size of the unit regions to calculate the Mahalanobis distance.

Incidentally, the program for the data processing unit 49 to carry out the functions of the determination method according to the invention may be mounted in the determination apparatus in advance. Alternatively, the particular program may be stored in various storage media adapted to record the program in a computer readable way. In the case where the program is used by being downloaded to the determination apparatus from an external source, however, the particular program is handled according to the invention in the same manner as if arranged in the determination apparatus in advance. The program and the various storage media for recording the program in a readable way are also included in the scope of the invention.

Figure 22:
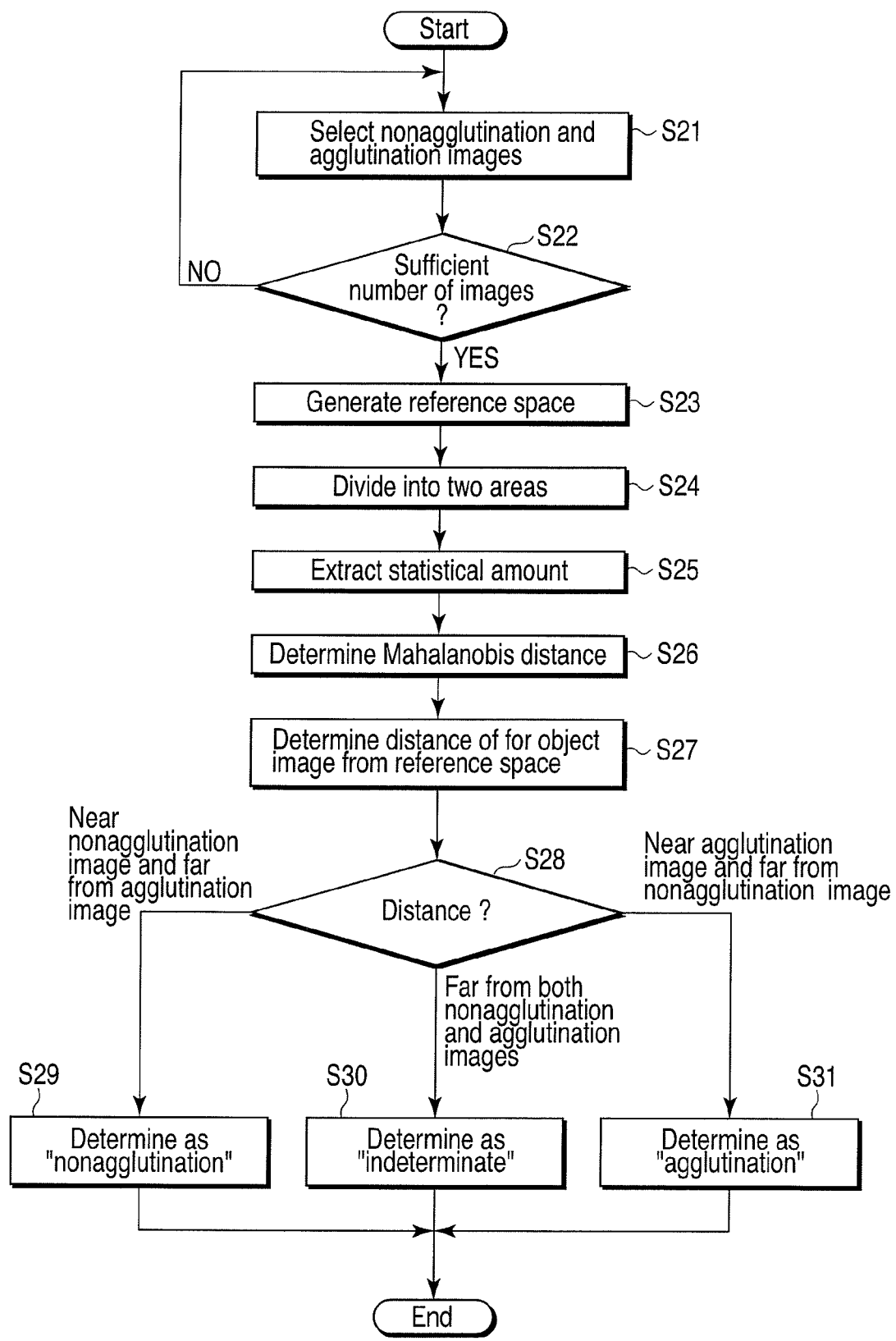
FIG. 22 is a flowchart showing one aspect of the invention.

Next, an example of the method of determining the agglutination pattern according to the invention using the automatic agglutination image determination apparatus shown in FIG. 21B is explained with reference to FIG. 22.

The determination method for the automatic agglutination image determination apparatus starts to be carried out.

In step S21, the nonagglutination or the agglutination used for generating a reference space is selected. First, the inspector inputs, from the input unit 40, the information on how many each of the nonagglutination images and the agglutination images used to generate a reference image are to be collected in what way and the conditions providing a standard for selecting a typical image, and instructs the processing unit to execute the process in keeping with the input conditions. In response to this instruction, the data processing unit 49 executes the processes of obtaining the data by the imaging operation of the imaging unit 45 of the automatic agglutination image determination apparatus, acquiring the data from an available database through a network, selecting the data from the images accumulated in the data processing unit 49 or outputting the image to the display unit 41 for selection by the inspector. In response to the instruction by the inspector through the input unit 40, the data processing unit 49 causes the display unit 41 to output the selected image. After image selection, the process proceeds to step S22.

In step S22, the data processing unit 49 determines whether the number of the images selected by the inspector in step S21 or by the data processing unit 49 has reached a preset number or not. In the case where the number of the images is insufficient, the process returns to step S21. In the case where the number of images is sufficient, on the other hand, the process proceeds to step S23. In the case where the preset number is unity (i.e., 1), however, the data processing unit 49 may advance the process from step S21 to step S23 skipping step S22.

Figure 8:
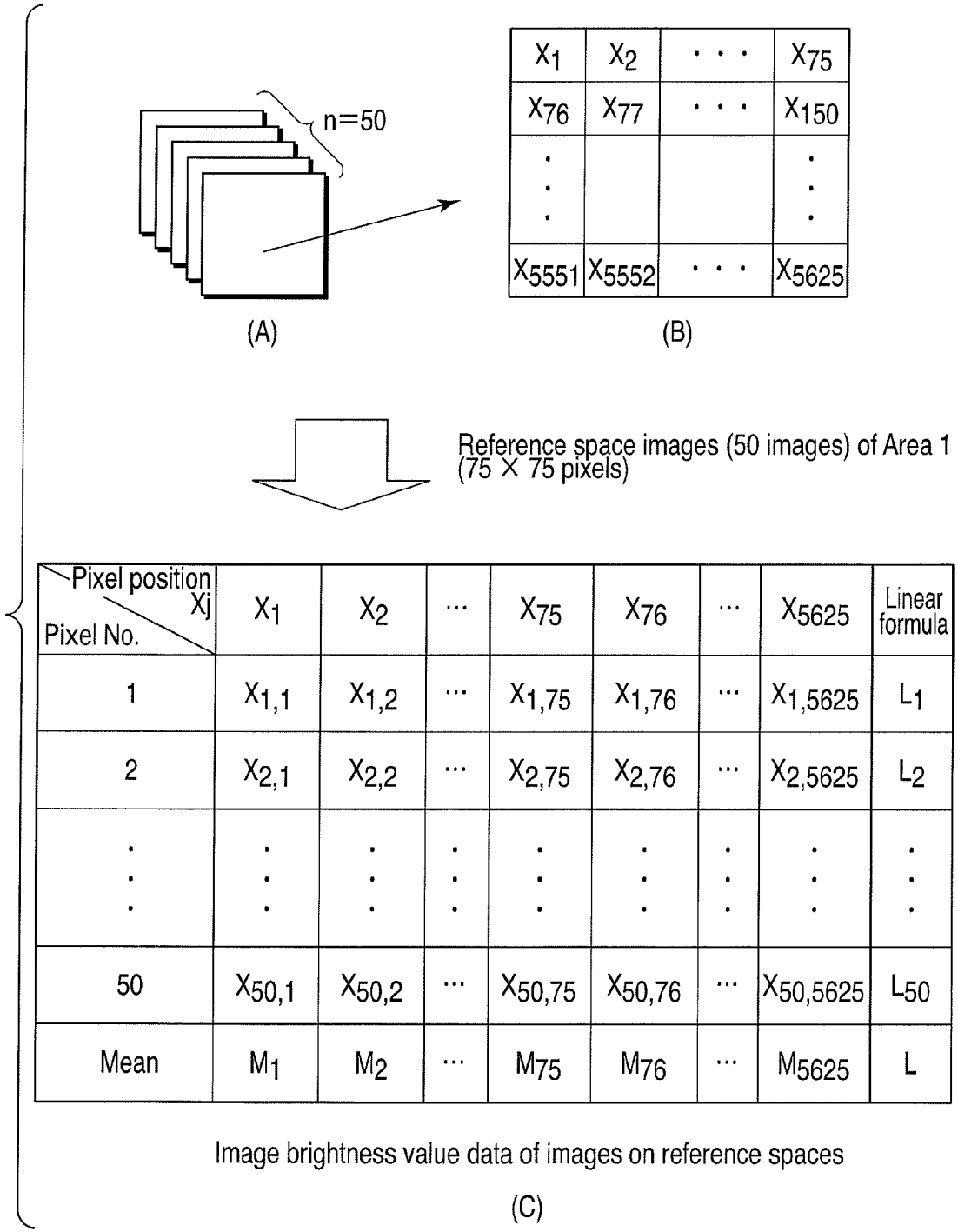
FIG. 8 is a diagram showing an example of a data processing operation used in the method according to the invention.

In step S23, the data processing unit 49 generates a reference space using the image selected in step S21, and executes the process to obtain the table shown in FIG. 8 using the equations shown in FIG. 9. The data including the result thus obtained is stored in the data processing unit 49 and/or output to the display unit 41, followed by proceeding to step S24.

In step S24, the data processing unit 49 sets the first and second regions of the image data obtained in step S23 according to the conditions set by the inspector in advance thereby to generate the image shown in FIG. 7, which is output to the display unit 41 and/or stored in the data processing unit 49, followed by proceeding to step S25.

In step S25, the data processing unit 49 calculates the statistical amount according to the equations shown in FIGS. 16 and 17 using the data on the reference space for each region set in step S24, generates the table showing the image, the region and the statistical amount in correspondence with each other as shown in FIG. 11, and displays the table on the display unit 41 and/or stores the table in the data processing unit 49, followed by proceeding to step S26.

In step S26, the data processing unit 49 calculates the Mahalanobis distance according to the equations shown in FIG. 20 based on the statistical amount obtained in step S25, generates a table in which the results obtained including the nonagglutination/agglutination, the region, the image and the Mahalanobis distance are indicated in correspondence with each other as shown in FIG. 12, and displays the table on the display unit 41 and/or stores the table in the data processing unit 49, followed by proceeding to step S27. Incidentally, steps S21 to S26 may be executed before the inspector conducts the agglutination test, in which case the inspector starts to carry out the determination method for the automatic agglutination image determination apparatus from step S27.

In step S27, the data processing unit 49 prepares an object image in accordance with a preprogrammed condition, determines the brightness value from the image, generates a table with the pixel position, the image number and the brightness value set in correspondence with each other as shown in FIG. 14, and generates another table with the nonagglutination/agglutination, the region, the image and the distance from the reference space set in correspondence with each other as shown in FIG. 15. The tables thus generated are displayed on the display unit 41 and/or stored in the data processing unit 49, followed by proceeding to step S28.

In step S28, the data processing unit 49 determines an object image by comparing the distance of the object image from the reference space based on the value stored beforehand in the data processing unit 49. In the case where the data processing unit 49 determines that the distance is short from the nonagglutination image and long from the agglutination image, the process proceeds to step S29, in which the image is determined as "nonagglutination" and displayed as "nonagglutination" on the display unit 41, followed by proceeding to the end of the process. In the case where the data processing unit 49 determines that the distance is long from both the nonagglutination image and the agglutination image, on the other hand, the process proceeds to step S30, in which the determination is made as "indeterminate" and the display unit 41 displays "indeterminate" or "?", followed by proceeding to the end of the process. Also, in the case where the data processing unit 49 determines that the distance is short from the agglutination image and long from the nonagglutination image, the process proceeds to step S31, in which the image is determined as "agglutination" and displayed as "agglutination" on the display unit 41, followed by proceeding to the end of the process. Further, in the case where the data processing unit 49 determines that the condition fails to be met that the distance is short from the nonagglutination image and long from the agglutination image and that the distance is short from the agglutination image and long from the nonagglutination image, then the process proceeds to step S30, in which the determination is made as "indeterminate" and the display unit 41 displays "indeterminate" or "?", followed by proceeding to the end of the process.

The determination result may be output to the display unit in the form of a table. This result may be displayed while at the same time being stored in the data processing unit 49.

According to a further aspect of the invention, there is provided an agglutination pattern determination method using the computer as described above. The flow of the procedure described above is only an example, and can be altered as required by those skilled in the art. Such an alteration is also covered by the scope of the invention.

Unlike in the aforementioned method in which the statistical amount is calculated for the brightness value, the statistical amount may alternatively be calculated using the image data other than the brightness value such as color data, or by use of the Mahalanobis distance.

Although the aforementioned example represents a case in which two unit regions are used, a similar process can be executed for one or three or more unit regions with equal effect.

As described above, according to the invention, there are provided a method, an apparatus and a program for automatic image determination and a recording medium whereby the determination can be made with a higher accuracy.

EXAMPLE 1

1. Background and Object of Experiment

The currently available Blood Transfusion Inspection Device PK7300 of Olympus intended for the blood test and the inspection for infectious diseases realizes the highest speed among similar products in the industry, the full automation of the inspection using a microplate developed by the company and an improved protocol check function in each analysis step. This device is currently employed at the Red Cross blood test centers in many countries and represents 80% of all the devices of this type used for the blood tests for transfusion in the world.

In the currently available devices, the result of the blood test is determined by processing the agglutination image pattern after reaction between the blood sampled from a subject and the reagent.

According to this embodiment, on the other hand, the MT system is used as a trial for the agglutination image pattern in the blood test.

2. Intended Technique

The appearance of the agglutination pattern of the blood that has reacted with the reagent is shown in FIG. 3. Once the blood and the reagent react with each other and agglutinate in the well of the microplate, the agglutinates are caught by the terrace of the well and assume a uniform image as a whole as shown in FIG. 3B. This is called the agglutination image. In the case where no agglutinate is formed, on the other hand, the blood cells slide down the terrace slope and gather at the center of the well thereby to form an image as shown in FIG. 3A. This is called the nonagglutination image.

A weak agglutination image resulting from the reaction at an intermediate level also exists. In the blood transfusion inspection device according to the invention, the blood group in an infectious disease is determined as negative or positive utilizing this difference in agglutination pattern. Typical agglutination and nonagglutination images captured by the CCD camera mounted on the upper part of the wells are observed as shown in FIGS. 3A and 3B.

In addition to these typical examples, various abnormal blood agglutination images are observed such as the "dropoff" as shown in FIG. 4A, the "milky fluid" as shown in FIG. 4B, the "foreign matter" as shown in FIG. 4C and the "deformation" as shown in FIG. 4D. These abnormal images are also desirably automatically determined with accuracy in accordance with each type thereof.

3. Evaluation Method 3-1 Concept of Determination Method

With regard to the intended technique as described in (2) above, the blood agglutination image according to this embodiment is considered to have two reference spaces. One is a typical agglutination image uniformly spread in the well by reaction between the blood and the reagent. The other is a typical nonagglutination image in which the blood cells are collected at the center of the well due to the total reaction failure between the blood and the reagent. According to this embodiment, an attempt is made to use the T method (i.e., the RS method or the RT method) using the reference signal-to-noise ratio among the various methods of the MT system.

The agglutination pattern is determined by calculating the Mahalanobis distance of an object image from the two reference spaces and using the relation between the two Mahalanobis distances thus calculated.

The concept of the determination method is shown in FIG. 1. The two reference spaces are defined as follows:

First reference space: a mass of typical nonagglutination images, and

Second reference space: a mass of typical agglutination images.

Thus, an image is determined as a nonagglutination image in the case where the Mahalanobis distance is short from the first reference space and long from the second reference space, while an image is determined as an agglutination image in the case where the Mahalanobis distance is long from the first reference space and short from the second reference space.

3-2 Calculation Method

For the two reference spaces described in (3-1) above, 50 images each 140 by 140 pixels converted to a grayscale (265 gradations) are prepared. The region of 75 by 75 pixels inscribed in the circular well is used for the calculation.

The calculation is made in the following order of steps:

(1) For each image in the reference space, the brightness values of 5625 (=75×75) pixels defined as shown in FIG. 8 are rearranged as shown in FIG. 8B, and the mean value M for each pixel and the linear formula L for each image are determined.

(2) For the images in the reference space, the statistical amounts $Y_1$, $Y_2$ are calculated from the reference signal-to-noise (SN) ratio $\eta$ and the sensitivity $\beta$.

(3) The mean values $m_1$, $m_2$ of the statistical amounts $Y_1$, $Y_2$ calculated in (2) are determined, so that the Mahalanobis distance D for the images inside the reference space and the Mahalanobis distance D for the images outside the reference space are calculated.

4. Result

The Mahalanobis distances for the agglutination image and the nonagglutination image inside the two reference spaces are shown in FIG. 23A, and the Mahalanobis distances for the agglutination image and the nonagglutination image outside the two reference spaces and a part of the Mahalanobis distances of various abnormal images are shown in FIG. 23B.

In order to study whether the agglutination image, the nonagglutination image and other various abnormal images can be determined from the relation between the two Mahalanobis distances, as shown in FIG. 25, the Mahalanobis distances for the first and second reference spaces are plotted on the ordinate and the abscissa, respectively, and indicated in two-dimensional distribution.

First, the distribution of the 50 image data used for the reference spaces is shown in FIG. 25. In the reference spaces, the 50 image data are distributed independently without superposition.

Figure 26:
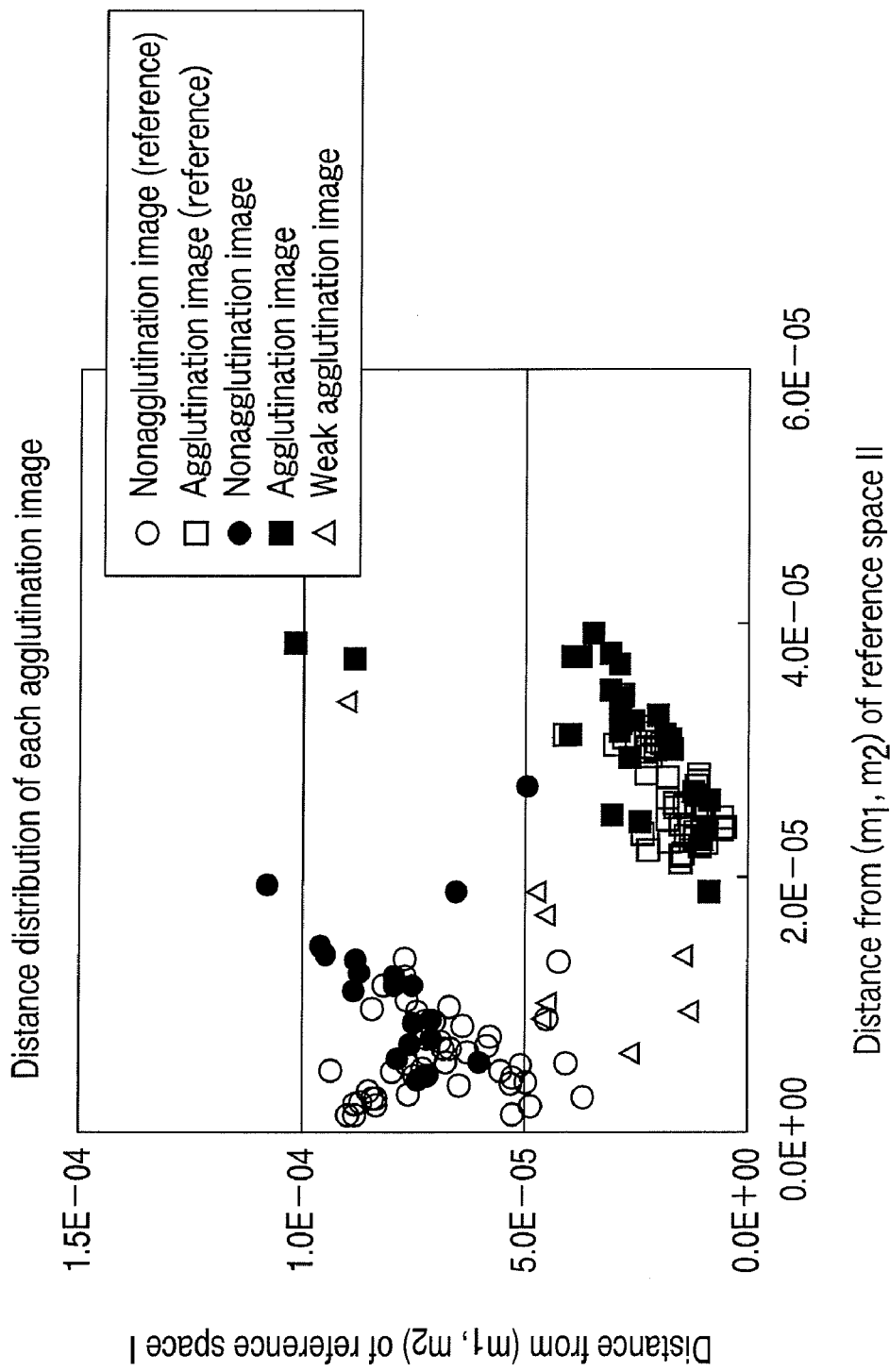
FIG. 26 is a diagram showing an example of a graph generated according to the invention.

The distribution of the agglutination image, the nonagglutination image and the weak agglutination image superposed outside the reference spaces is shown in the graph of FIG. 26. The agglutination image and the nonagglutination image outside the reference spaces, though mixed with bubbles and not typical ones, are desirably determined as the agglutination image or the nonagglutination image. The weak agglutination image, on the other hand, is intermediate in reaction, and therefore, desirably distributed between the agglutination image and the nonagglutination image. FIG. 26 indicates that the image outside the reference spaces, though generally superposed on the data inside the reference spaces, has a part of data considerably separate from the reference spaces. As a result of studying these images, it has been found that the nearer an image to a typical one, the nearer the distribution in the reference spaces, and the data mixed with bubbles has a distribution separate from the reference space. Also, the weak agglutination image is substantially correlated with the Mahalanobis distance from each reference space, and distributed continuously in accordance with the strength of agglutination in a region intermediate between the two regions where the agglutination image and the nonagglutination image are distributed. This indicates that even for the agglutination pattern with the intermediate agglutination reaction, the determination result can be divided by setting plural intermediate threshold values in stages and comparing each threshold value with the Mahalanobis distance. The number and the value of each threshold in the stages can be set by the inspector inputting them appropriately though an appropriate input unit while confirming them on the display screen. As described above, unlike the prior art in which a determination algorithm unique to each image division is required to be determined by trials and errors, the invention can provide a determination method and an apparatus in which the intermediate image can be easily determined simply by dividing the threshold value obtained from the reference spaces into stages.

Figure 27:
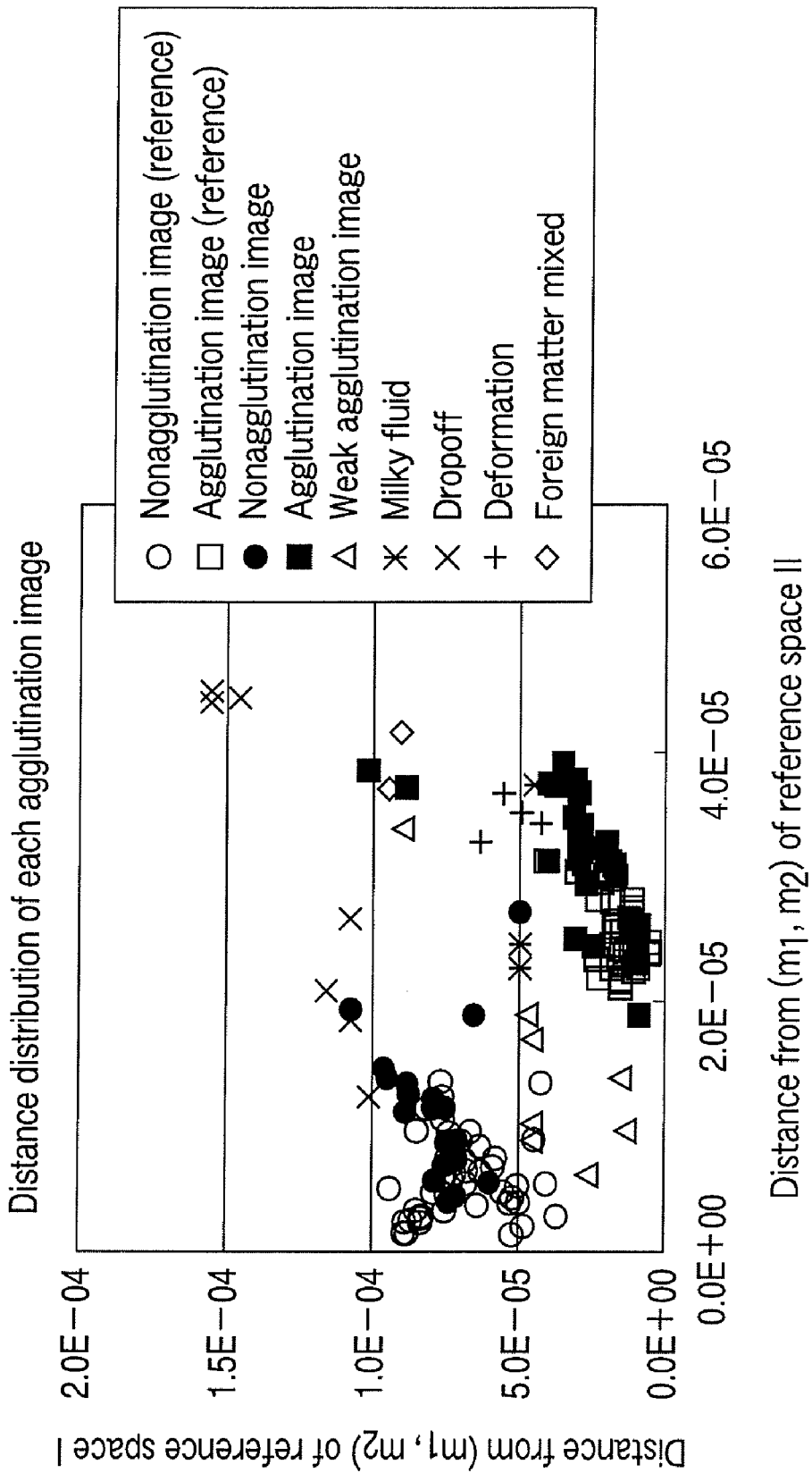
FIG. 27 is a diagram showing an example of a graph generated according to the invention.

Next, a graph with the distribution of various abnormal images superposed one on another is shown in FIG. 27. Each image, though originally expected to be distributed independently free of superposition with the agglutination image or the nonagglutination image, is finally found to be superposed with the agglutination image or the nonagglutination image outside the reference spaces and cannot be easily determined independently.

From the foregoing study, it has been found that the distribution of the Mahalanobis distances from the two reference spaces can be determined as the agglutination image, the nonagglutination image and other images according to a certain threshold value.

EXAMPLE 2

Figure 28:
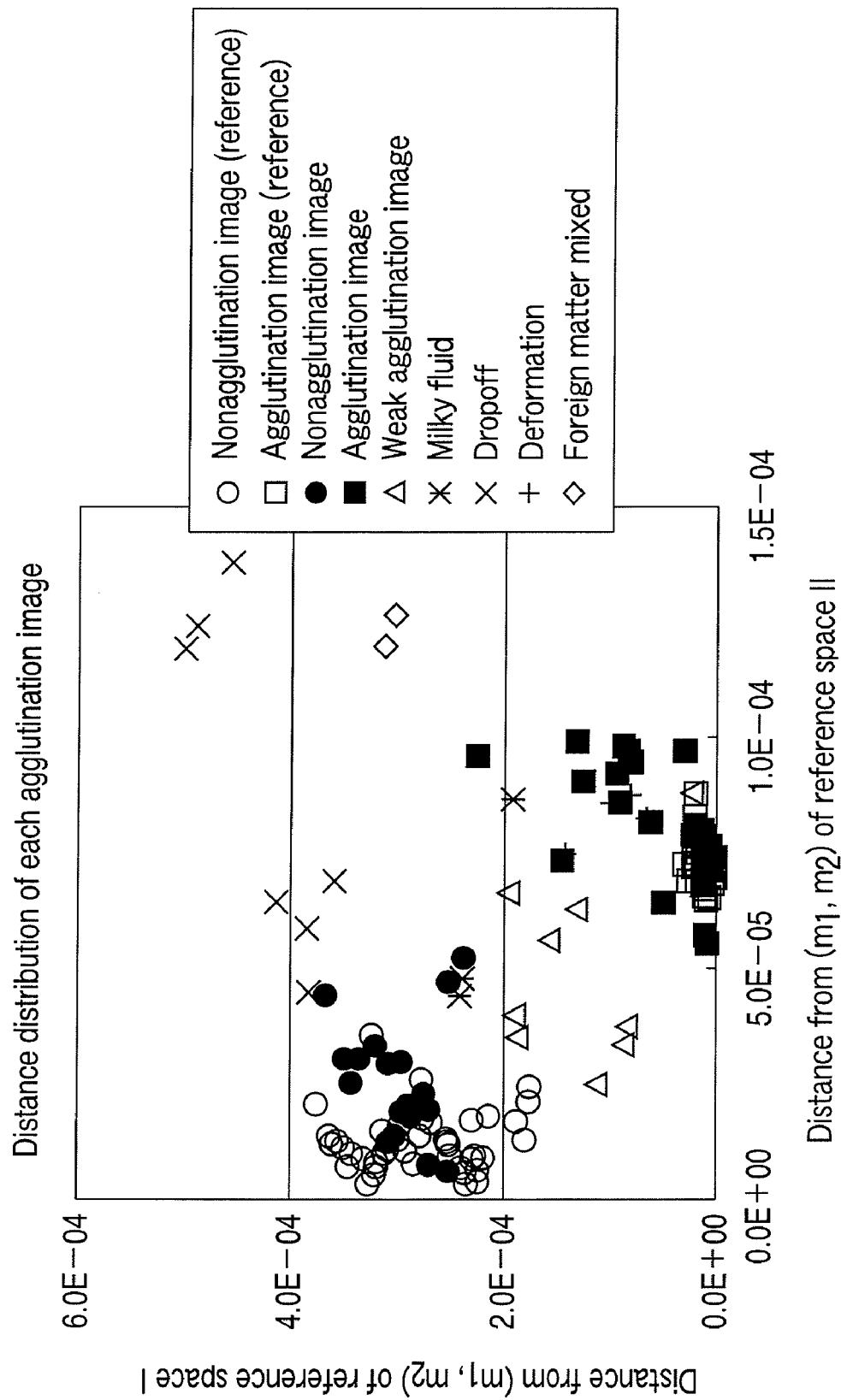
FIG. 28 is a diagram showing an example of a graph generated according to the invention.

As to the regions used for the calculation, as shown in FIG. 7, the region indicated in Example 1 is defined as a first region, and an region having 45 by 45 pixels in the well as a second region. Then, the analysis is conducted in the same manner as in Example 1. The result is shown in FIG. 28.

The agglutination image, the nonagglutination image and the weak agglutination image have a similar distribution to the result of the study made about the region having 75 by 75 pixels. Also, among the various abnormal images, "dropoff" and "foreign matter" are independently distributed, and as compared with the region having 75 by 75 pixels, a desirable result is obtained from the study.

The fact described above indicates that the abnormal images can also be classified by differentiating the area of each unit region. Especially, by reducing the area of the second region as compared with the area of the first region as in Example 2, the abnormal images often observed in the first region can be probably separated. In addition to the determination for agglutination and nonagglutination, an apparatus is expected to be realized in which the presence or absence of an abnormal image is determined, the result of classification thereof is added, and the agglutination pattern for an abnormal image is not determined (or left without determination). The area of the unit region can be changed by increasing (for example, by dividing the regions or reducing the area of each region by additionally setting regions yet to be set) or decreasing (for example, by merging the regions or increasing the area of each region by deleting the existing regions) the number of the unit regions set through the input unit.

In the prior art, the determination algorithm unique to each image desired to be divided is required to be determined by trials and errors. According to this embodiment, however, as described above, a determination method and apparatus are provided which can determine abnormal images easily by simply changing the unit regions with respect to the reference space.

Incidentally, from another viewpoint, Example 2 contributes to the improvement in the ability to classify the intermediate images. Specifically, by changing the area of the unit region (in the case under consideration, by reducing the area of the unit region in such a manner as to reduce the image portion unique to the first reference space corresponding to the typical nonagglutination image), as shown in FIG. 28, the distribution of the data on the intermediate image can be obtained which converges substantially linearly between the agglutination and the nonagglutination.

EXAMPLE 3

In Examples 1 and 2 described above, the MTA method is used to calculate the Mahalanobis distance. Also, the Mahalanobis distance is calculated and the image determined using the MT method, with the result that the image can be determined in the same way as the MTA method.

EXAMPLE 4

In the method according to the invention, the column agglutination technique (generally called "CAT") can be used.

According to the agglutination test, the agglutinate particles are separated from the nonreactive component using the filter for immunoassay. This method uses a vessel in which gels or glass bead particulates are accommodated in a microcolumn together with a reagent such as anti-IgG. An example is shown in FIG. 29A. A microcolumn comprising plural columns is shown in FIG. 29A. Each column contains the gels or glass bead particulates. In this microcolumn, the centrifugal separation causes the reaction strength to be reflected in the particle distribution as shown in FIG. 29A. The column to the extreme left shows a typical agglutination image with an agglutinate mass located in the upper part of the gels, while the column to the extreme right shows a typical nonagglutination image with the blood cell particles collected on the bottom of the gels.

An explanation is further made with reference to one of the columns of this microcolumn. Refer to FIG. 29B.

The particles with the red blood cells or a binder are arranged in the reaction chamber above the column, and during the centrifugal separation, the blood cells or the particles are mixed with a reagent 56 in the column. Upon occurrence of the reaction in the column in the process, the blood cells are partially or wholly agglutinated and captured by the bead region after centrifugal separation. In the case where no reaction occurs, on the other hand, the nonagglutinate blood cells are moved to the bottom of the column by centrifugal force. The reaction result can be determined by the particle distribution obtained in the microcolumn after centrifugal separation. For example, the reaction or nonreaction can be visually observed, and in the case where the reaction occurs, the strength of the reaction can be visually determined.

FIG. 29B shows one column of the microcolumn. The column 50 is filled with a gel in portions 51 to 53, and the particles of a size passable through the gaps of the gel are moved to a bottom portion 55 by centrifugal separation in the column. In the case where a strong agglutination occurs, therefore, an agglutinate mass stays in a portion 54 above the gel. Depending on the agglutination strength, the agglutinate mass stays in any one of the first gel 51, the second gel 52, the third gel 53 or a combination thereof. In the case where no agglutination occurs, on the other hand, the particles are moved to the bottom portion 55.

With regard to the result of the agglutination reaction conducted in this reaction vessel, therefore, the unit regions can be set and the method according to the invention can be carried out in the manner described above.

Specifically, a first region is set as a combination of the first gel 51 and the second gel 52, and a second region as the portion of the third gel 53. For other than this setting, like in Example 1 or 2 described above, an image is obtained, the statistical amount is extracted and the required distance is calculated, so that the image can be determined by the MT or MTA method.

Although the aforementioned example includes two unit regions, the number of unit regions may be three or more or one. As another alternative, the setting of the first and second regions may be changed. Also, the bottom surface of each of plural columns of a card-type microcolumn may be flat, U-shaped or V-shaped.

EXAMPLE 5

An application of Example 4 is described below. Refer to FIG. 29B. In FIG. 29B, a first gel region 51, a second gel region 52, a third gel region 53 and a fourth region as a combination of the first to third gel regions 51 to 53 are set as unit regions. In the case where the Mahalanobis distance of each of the first to third regions 51 to 53 is in a predetermined threshold range, the image is determined as a normal image, and the agglutination or nonagglutination is determined by the Mahalanobis distance of the fourth region. In the case where the Mahalanobis distance of each of the first to third regions 51 to 53 is outside the predetermined threshold range, on the other hand, the image is determined as an abnormal reaction image and left without being determined.

Further advantages and modifications of the invention will be easily understood by those skilled in the art. The present invention according to a wider aspect, therefore, is not limited to the representative aspect specifically described in detail above. This invention can thus be modified variously without departing from the spirit and scope of the invention generally apparent from the appended claims and the equivalencies thereof.

What is claimed is:

1. A method of determining an agglutination pattern type for a pattern formed in a reaction vessel, comprising:
(A) setting a plurality of reference spaces based on one or a plurality of types of typical reaction images;
(B) setting one or a plurality of types of unit regions in each of the reference spaces obtained in (A) and determining a Mahalanobis distance for each unit region,
wherein the one or a plurality of types of unit regions comprise a first unit region, the first unit region includes a collected portion at which particles are most concentrated area and a reaction image portion other than the collected portion, wherein the collected portion and the reaction image portion other than the collected portion are in the same typical reaction image of a typical agglutination image or a typical nonagglutination image;
(C) setting a threshold value from each of the Mahalanobis distances obtained in (B);
(D) setting one or a plurality of unit regions for a reaction image to be determined as an object image and determining the Mahalanobis distance for each of the unit regions; and
(E) determining the agglutination pattern type for the object image by comparing the threshold value set in (C) with the distances determined in (D).

2. A method of determining an agglutination pattern type for a pattern formed in a reaction vessel, comprising:
(A) setting a plurality of reference spaces based on one or a plurality of types of typical reaction images;
(B) setting one or a plurality of unit regions for each of the reference spaces set in (A) and extracting a feature amount for each of the unit regions,
wherein the one or a plurality of types of unit regions comprise a first unit region, the first unit region includes a collected portion at which particles are most concentrated area and a reaction image portion other than the collected portion, wherein the collected portion and the reaction image portion other than the collected portion are in the same typical reaction image of a typical agglutination image or a typical nonagglutination image;
(C) setting a threshold value by determining a Mahalanobis distance of a reaction image set in a reference space from the reference space based on each of the feature amounts obtained in (B);
(D) setting one or a plurality of unit regions in the reaction images to be determined, and extracting the feature amount of each of the unit regions;
(E) determining the Mahalanobis distance of each reaction image from the reference space based on the feature amount obtained in (D); and
(F) determining the agglutination pattern type for the object image by comparing the threshold value set in (C) with the distance determined in (E).

3. The method according to claim 1, wherein the steps (A) to (C) are executed in advance, and based on the setting thus obtained, the steps (D) to (E) are carried out repeatedly.

4. The method according to claim 1, wherein a plurality of unit regions are set in the (B) and at least two of said plurality of unit regions have different areas.

5. The method according to claim 1, wherein agglutination is determined based on a relation between the Mahalanobis distances of the intended reaction image determined from one or a plurality of regions in one or a plurality of reference spaces by comparing the threshold value and the distance with each other.

6. The method according to claim 1, wherein agglutination is determined based on the integrated Mahalanobis distance of the intended reaction image determined from one or a plurality of regions in one or a plurality of reference spaces by comparing the threshold value and the distance with each other.

7. A method of determining an agglutination pattern type for a pattern formed in a reaction vessel, comprising:
(a) selecting a nonagglutination image for a first reference space and an agglutination image for a second reference space;
(b) setting one or a plurality of types of unit regions for each of the image for the first reference space and the image for the second reference space, and extracting a statistical amount,
wherein the one or a plurality of types of unit regions comprise a first unit region, the first unit region includes a collected portion at which particles are most concentrated area and a reaction image portion other than the collected portion, wherein the collected portion and the reaction image portion other than the collected portion are in the same typical reaction image of a typical agglutination image or a typical nonagglutination image;
(c) determining a Mahalanobis distance for the first reference space from the statistical amount of each of the unit region of the first reference space and a Mahalanobis distance for the second reference space from the statistical amount of each of the unit region of the second reference space;

(d) setting one or a plurality of types of unit regions for an object image and extracting the statistical amount for each unit region, (e) determining a distance of the object image from the first reference space and the second reference space based on the statistical amounts obtained in (d) and the Mahalanobis distance; and (f) determining the agglutination pattern type based on the distance obtained in (e).

8. The method according to claim 7, wherein the steps (a) to (c) are executed in advance, and based on the distance obtained thereby, the steps (d) to (f) are repeatedly executed.

9. The method according to claim 7, wherein the unit regions further comprise a second region for the first and second reference space and the object image.

10. The method according to claim 9, wherein the determination of (f) is effected based on the relation of the first region of the object image with the first region of the first reference space and the first region of the second reference space, and the relation of the second region of the object image with the second region of the first reference space and the second region of the second reference space.

11. The method according to claim 9, wherein the determination of (f) is effected based on the relation of the integrated Mahalanobis distance of the first region of the first reference space and the first region of the second reference space with the first region of the object image, and the relation of the integrated Mahalanobis distance of the second region of the first reference space and the second region of the second reference space with the second region of the object image.

12. The method according to claim 1, wherein all the images are converted to a grayscale before being used.

13. The method according to claim 1, wherein the Mahalanobis distance is determined by selected one of an MTA method and an MT method using a brightness value of each pixel of the image.

14. The method according to claim 1, wherein the nonagglutination image is an image with particles collected at a center of the bottom surface of the reaction vessel, and the agglutination image is an image with the particles existing over the entire bottom surface of the reaction vessel.

15. The method according to claim 1, wherein the reaction vessel comprises a tubular portion, and the nonagglutination image is formed with the particles collected at the lowest part of the tubular portion and the agglutination image is formed with the particles collected in the upper part of the tubular portion.

16. The method according to claim 1, wherein one side of the reaction vessel is in solid phase to form a specific bonding pair therein.

17. The method according to claim 1, wherein the agglutination reaction is a blood agglutination reaction.

18. The method according to claim 1, wherein at least one of the unit regions is defined by selected one of a polygon and a circle of the reaction image containing the center of the reaction vessel.

19. The method according to claim 12, wherein the first region is defined by selected one of a polygon and a circle of the image inscribed in an inner wall of the vessel, and the second region is defined by selected one of a polygon and a circle concentric with selected one of the polygon and the circle of the first region.

20. The method according to claim 19, wherein the first region and the second region are defined by shapes similar to each other.

21. The method according to claim 9, wherein the first region and the second region have different areas.

22. The method according to claim 9, wherein the area of the first region is larger than that of the second region.

23. An apparatus which automatically determines an agglutination pattern type for an object formed in a reaction vessel, comprising:

a data processing unit configured to make determination according to a criterion based on a Mahalanobis distance for a first reference space corresponding to at least one typical nonagglutination image and a Mahalanobis distance for a second reference space corresponding to at least one typical agglutination image; and an image acquisition unit configured to acquire a reaction image of the object to be transmitted to the data processing unit, wherein the Mahalanobis distance for the first reference space is determined from one or a plurality of types of unit regions contained in the first reference space, the Mahalanobis distance for the second reference space is determined from one or a plurality of types of unit regions contained in the second reference space, wherein the one or a plurality of types of unit regions for the first and second reference space each comprise a first unit region, the each first unit region including a collected portion at which particles are most concentrated area and a reaction image portion other than the collected portion, wherein the collected portion and the reaction image portion other than the collected portion are in the same typical reaction image of a typical agglutination image or a typical nonagglutination image; and wherein the data processing unit determines the agglutination pattern type according to the computation result based on the Mahalanobis distance.

24. The automatic determination apparatus according to claim 23, wherein the criterion has a plurality of stages of threshold values corresponding to the Mahalanobis distance for the first reference space and the second reference space, and based on each threshold value, the pattern of an intermediate agglutination between agglutination and nonagglutination is classified.

25. The automatic determination apparatus according to claim 23, wherein the criterion has such a threshold value that a given agglutination far from the first reference space and near the second reference space is classified as agglutination, and a given agglutination near the first reference space and far from the second reference space is classified as nonagglutination.

26. The automatic determination apparatus according to claim 23, further comprising an input unit configured to set at least one of the number and the area of the unit region for calculating the Mahalanobis distance.

27. The automatic determination apparatus according to claim 23, further comprising a display unit configured to display an agglutination image group and a nonagglutination image group constituting candidates for the first and second reference spaces, and an input unit configured to designate at least selected one of an image and the number of images based on the image group displayed on the display unit.

28. A non-transitory computer readable recording medium recording a program for determining an agglutination pattern type for a pattern formed in a reaction vessel, causes a computer to function as:

a first data processing unit configured to make determination according to a stored criterion based on the Mahalanobis distances for a first reference space corresponding to at least one typical nonagglutination image and a Mahalanobis distance for a second reference space corresponding to at least one typical agglutination image, wherein the Mahalanobis distance for the first reference space is determined from one or a plurality of types of unit regions contained in the first reference space, the Mahalanobis distance for the second reference space is determined from one or a plurality of types of unit regions contained in the second reference space, wherein the one or a plurality of types of unit regions for the first and second reference space each comprise a first unit region, the each first unit region includes a collected portion at which particles are most concentrated area and a reaction image portion other than the collected portion, wherein the collected portion and the reaction image portion are in the same typical reaction image of a typical agglutination image or a typical nonagglutination image; and an image acquisition unit configured to acquire a reaction image of an object and transmit the acquired reaction image to the data processing unit;

a second data processing unit configured to compute the Mahalanobis distance based on the reaction image obtained by the image acquisition unit; and a third data processing unit configured to determine the agglutination pattern type for the object by comparing the criterion with the Mahalanobis distance based on the reaction image.

29. The program according to claim 28, wherein in order to classify an intermediate agglutination pattern between agglutination and nonagglutination, the stored criterion includes a plurality of stages of threshold values corresponding to the Mahalanobis distance to the first and second reference spaces.

30. The program according to claim 28, wherein in order to determine the agglutination pattern type, the stored criterion includes a threshold value for classifying the agglutination pattern as an agglutination in the case where the distance is long from the first reference space and short from the second reference space, and classifying the agglutination pattern as a nonagglutination in the case where the distance is short from the first reference space and long from the second reference space.

31. The program according to claim 28, wherein the computer further functions as an input unit configured to set at least one of the number and the area of the unit regions for calculating the Mahalanobis distance.

32. The program according to claim 28, wherein the computer is caused to function further as:

a display unit configured to display an image group of agglutination and nonagglutination as candidates for the first and second reference spaces; and an input unit configured to designate at least one of an image and the number of images based on the image group displayed on the display unit.

33. A non-transitory computer readable recording medium having recorded therein the program according to claim 28 in a way readable by the computer.

* * * * *